US006534628B1

(12) United States Patent
Nilsson et al.

(10) Patent No.: US 6,534,628 B1
(45) **Date of Patent: *Mar. 18, 2003**

(54) BACTERIAL RECEPTOR STRUCTURES

(75) Inventors: Björn Nilsson, Sollentuna (SE); Per-Åke Nygren, Skarpnäck (SE); Mathias Uhlén, Uppsala (SE)

(73) Assignee: Biovitrum AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/082,468

(22) Filed: May 21, 1998

Related U.S. Application Data

(63) Continuation of application No. 08/669,360, filed as application No. PCT/SE95/00034 on Jan. 16, 1995, now Pat. No. 5,831,012.

(30) Foreign Application Priority Data

Jan. 14, 1994 (SE) ............................................. 9400088

(51) Int. Cl.[7] .......................... C07K 1/00; C07K 14/00; C07K 17/00; C12N 1/20; G01N 33/543

(52) U.S. Cl. ....................... 530/350; 530/300; 530/825; 530/402; 530/387.1; 530/386; 435/7.1; 435/172.1; 435/69.7; 435/882; 435/883; 435/320.1; 436/536; 436/501; 436/518

(58) Field of Search ................................ 530/350, 300, 530/825, 402, 387.1, 386; 435/7.1, 320.1, 172.1, 69.7, 882, 883; 436/536, 501, 518

(56) References Cited

U.S. PATENT DOCUMENTS

| | | | | |
|---|---|---|---|---|
| 4,879,213 | A | * | 11/1989 | Fox et al. |
| 4,954,618 | A | * | 9/1990 | Fahnestock |
| 5,084,559 | A | * | 1/1992 | Profy |
| 5,229,492 | A | * | 7/1993 | Fahnestock |
| 5,312,901 | A | * | 5/1994 | Fahnestock |
| 5,783,415 | A | * | 7/1998 | Lee et al. |
| 5,831,012 | A | * | 11/1998 | Nilsson et al. |
| 6,025,166 | A | * | 2/2000 | Presta et al. |
| 6,027,927 | A | * | 2/2000 | Presta et al. |

OTHER PUBLICATIONS

Nord et al, Nature Biotechnology, 15/8:775–777, Aug. 1997.*

Nord et al, Protein Engineering, 8/6:601–608, 1995.*

Cedergren et al. Prot. Engineering 6/4:441–448, 1993.*

* cited by examiner

*Primary Examiner*—Nita Minnifield
(74) *Attorney, Agent, or Firm*—Fish & Richardson P.C.

(57) ABSTRACT

Novel proteins obtainable by mutagenesis of surface-exposed amino acids of domains of natural bacterial receptors, said proteins being obtained without substantial loss of basic structure and stability of said natural bacterial receptors; proteins which have been selected from a protein library embodying a repertoire of said novel proteins; and methods for the manufacture of artificial bacterial receptor structures.

46 Claims, 19 Drawing Sheets

| Ss | E | A1 | B1 | A2 | B2 | A3 | S | C1 | D1 | C2 | D2 | C3 | W | M |

Figure 1A:
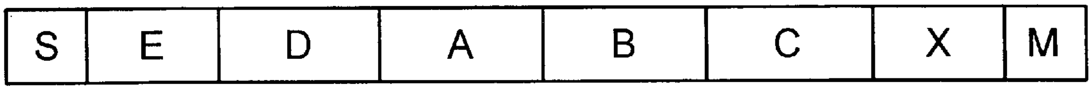

| | |
|---|---|
| ZLIB-1 | BIOTIN - 5' - GCG CAA CAC GAT GAA GCC GTA GAC AAC AAA TTC AA - 3' |
| ZLIB-2 | 5' - TTC TT GTT GAA TTT GTT GTC TAC GGC TTC ATC GTG TTG CGC - 3' |
| ZLIB-3 | 5' - CG CGC GCG TCT CAC GCG GCG CAA CAC GAT GAA GCC GTA - 3' |
| ZLIB-4 | 5' - A AGC CAA AGC GCT AAC TTG CTA GCA GGG - 3' |
| ZLIB-5 | 5' - CCC CCC TGC TAG CAA GTT AGC GCT TTG GCT TGG GTC ATC - 3' |
| ZLIB-6 | 5' - C GCG TGA ATT CTG CTA GCA GAA GCT AAA AAG CTA AAT GAT CGT CAG GCG CCG AAA AGC - 3' |
| ZLIB-7 | 5' - T CGA GCT TTT CGG CGC CTG AGC ATC ATT TAG CTT TTT AGC TTC TGC TAG CAG AAT TCA - 3' |
| LONG BRIDGE | 5' - TTG TTC TTC GTT TAA GTT AGG TAA ATG TAA GAT CTC - 3' |
| ACID-1 | C AAA GAA $G^{CA}_{AC}$ CAA $G^{CA}_{AC}$ GCG TTC $G^{CA}_{AC}$ GAG ATC TTA CAT TTA CCT A - 3' |
| ACID-2 | 5' - AC TTA AAC GAA GAA CAA $G^{CA}_{AC}$ AAC GCC TTC ATC CAA AGT TTA $G^{CA}_{AC}$ GAT GAC CC - 3' |
| DEGEN-2 | 5' - AC TTA AAC $NN^{G}_{T}$ $NN^{G}_{T}$ CAA $NN^{G}_{T}$ $NN^{G}_{T}$ GCC TTC ATC $NN^{G}_{T}$ AGT TTA $NN^{G}_{T}$ GAT GAC CC - 3' |
| DEGEN-1 | 5' - C AAA GAA $NN^{G}_{T}$ $NN^{G}_{T}$ $NN^{G}_{T}$ $NN^{G}_{T}$ GCG $NN^{G}_{T}$ GAG ATC $NN^{G}_{T}$ $NN^{G}_{T}$ TTA CCT A - 3' |
| BRIDGE | 5' - GTT TAA GTT AGG TAA - 3' |

FIG. 6

```
1                                       9         11           14
GTA GAC AAC AAA TTC AAC AAA GAA GAC CAA GCA GCG TTC GAC NAG ATC TTA CAT TTA CCT AAC TTA AAC
GTA GAC AAC AAA TTC AAC AAA GAA GAC CAA GAC GCG TTC GAC GAG ATC TTA CAT TTA CCT AAC TTA AAC
Acc I

               27                                      35
GAA GAA CAA GAC AAC GCC TTC ATC CAA AGT TTA GCA GAT GAC CCA AGC CAA GCT AAC TTG CTA GC
GAA GAA CAA GAA AAC GCC TTC ATC CAA AGT TTA GCA GAT GAC CCA AGC CAA GCT AAC TTG CTA GC
                                                                                Nhe I
```

FIG. 7

| | | 10 | | | | | 20 | | | | 30 | | | | 40 50 |
|---|---|---|---|---|---|---|---|---|---|---|---|---|---|---|---|
| Z: | VDNKFNKE | QQN | A | FY | EI | LH | LPNLN | EE | Q | RN | AFI | Q | SL | K | DDPSQSANLLAEAKKLNDAQAPK |
| 1: | -------- | AGI | - | IS | -- | WA | ----- | CS | - | QM | --- | H | -- | H | ----------------------- |
| 2: | -------- | MTA | - | GL | -- | WV | ----- | RT | - | TM | --- | A | -- | I | ----------------------- |
| 3: | -------- | TVB | - | DS | -- | TR | ----- | RW | - | VK | --- | M | -- | S | ----------------------- |
| 4: | -------- | A-A | - | RP | -- | VG | ----- | DL | - | SP | --- | S | -- | L | ----------------------- |
| 5: | -------- | -MG | - | RR | -- | VL | ----- | NG | - | AR | --- | G | -- | H | ----------------------- |
| 6: | -------- | ESC | - | VQ | -- | GE | ----- | A- | - | GA | --- | F | -- | Q | ----------------------- |
| 7: | -------- | -AA | - | RR | -- | HL | ----- | VQ | - | MG | --- | I | -- | R | ----------------------- |
| 8: | -------- | AGR | - | L- | -- | -D | ----- | -N | - | QG | --- | N | -- | - | ----------------------- |
| 9: | -------- | MGI | - | QS | -- | VY | ----- | VR | - | GF | --- | S | -- | L | ----------------------- |
| 10: | -------- | LB- | - | LF | -- | -E | ----- | KT | - | -F | --- | R | -- | R | ----------------------- |
| 11: | -------- | VRY | - | RL | -- | GP | ----- | WT | - | PY | --- | W | -- | D | ----------------------- |
| 12: | -------- | TWM | - | CQ | -- | AV | ----- | KT | - | HL | --- | M | -- | S | ----------------------- |
| 13: | -------- | APF | - | GR | -- | QR | ----- | PM | - | -Q | --- | M | -- | S | ----------------------- |
| 14: | -------- | PFD | - | -L | -- | QF | ----- | LM | - | MR | --- | R | -- | G | ----------------------- |
| 15: | -------- | H-G | - | HD | -- | PR | ----- | AY | - | AI | --- | V | -- | E | ----------------------- |
| 16: | -------- | KRI | - | GC | -- | AC | ----- | AR | - | SA | --- | L | -- | V | ----------------------- |
| 17: | -------- | EMB | - | HE | -- | BK | ----- | KT | - | WG | --- | V | -- | P | ----------------------- |
| 18: | -------- | -BD | - | PS | -- | D- | ----- | FL | - | CG | --- | T | -- | A | ----------------------- |
| 19: | -------- | TLR | - | QT | -- | ES | ----- | MG | - | ML | --- | V | -- | S | ----------------------- |
| 20: | -------- | G-A | - | SA | -- | GW | ----- | WC | - | DB | --- | A | -- | T | ----------------------- |

FIG. 14A

BACTERIAL RECEPTOR STRUCTURES

This application is a continuation of application Ser. No. 08/669,360 filed Aug. 15, 1996, now U.S. Pat. No. 5,831, 012; which is a §371 of PCT/SE95/00034 filed Jan. 16, 1995; which claims priority to Swedish Application Serial No. 9400088-2 filed Jan. 14, 1994.

The present invention relates to new bacterial receptor structures originating from natural bacterial receptor structures which have been modified in regard to amino acid residues involved in the original interaction function, whereby said original interaction function has been substantially inhibited and replaced by a modified interaction function directed to a desired interaction partner.

Several bacteria known to invade mammals have evolved surface proteins capable of binding to a variety of substances including host specific carbohydrates and proteins. Several such receptors from Gram-positive bacterial pathogens have been isolated and characterized in detail as will be shown below. Most well-characterized are the Fc receptors, named after the capability of binding to the constant Fc part of IgG. Based on binding experiments to IgG from various mammalian sources, and subclasses thereof, Fc receptors have been divided into six types I–VI. The receptor from *S.aureus,* protein A [SPA], defining the type I receptor, has been the subject of immense studies.

Figure 2A:
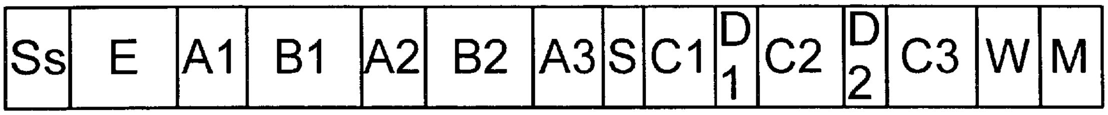

SPA binds IgG from most mammalian species, including man. Of the four subclasses of human IgG, SPA binds to IgG1, and IgG4 but shows very weak or no interaction with IgG3 [Eliasson, M. et al, 1989 J.Biol.Chem. 9:4323–4327]. This pseudoimmune reaction has been used for more than 20 years for the purification and detection of antibodies in diagnostic, research and therapeutic applications. Cloning, sequencing and *Escherichia coli* expression of defined fragments of the SPA gene revealed a highly repetitive organization, with five IgG binding domains [E-D-A-B-C], a cell wall spanning region and membrane anchoring sequence [XM] [Uhlén, et al, 1984 J.Biol.Chem. 259:1695–1702; Moks, T. et al, 1986 Eur.J.Biochem. 156:637–643]. A vast number of plasmid vectors have been constructed, allowing gene fusions to different fragments of the gene for the purpose of fusion protein production in different hosts [Nilsson B. and Abrahmsén, L. 1990 Meth. Enz. 185:144–161] (FIG. 2*a*).

The structure for a complex between human Fc [IgG1] and a single domain [B] of SPA has been determined by X-ray crystallography at a resolution of 2.8 Å [Deisenhofer, J. et al 1981 Biochemistry 20:2361–2370]. Based on this structure and additional information from NMR experiments, the B domain can be viewed as a compact structure consisting of three anti-parallel α-helices connected with loops. In the Fc binding, which is of both electrostatic and hydrophobic nature, only side chains of residues from helices 1 and 2 are involves, whilst the third helix is not participating in the binding. Based on this domain B, a synthetic IgG-binding domain [Z] [Nilsson, B. et al 1987 Prot,Eng. 1:107–113] has been constructed, suitable as fusion partner for the production of recombinant proteins which allows purification by IgG affinity chromatography. The high solubility and the stable structure of the Z domain has been utilized for production, purification and renaturation of a large number of recombinant proteins. [Josephsson, S. and Bishop, R. Trends Biotechnol. 6:218–224; Samuelsson, E. et al 1991 Bio.Technol. 9:363–366]

Figure 2B:
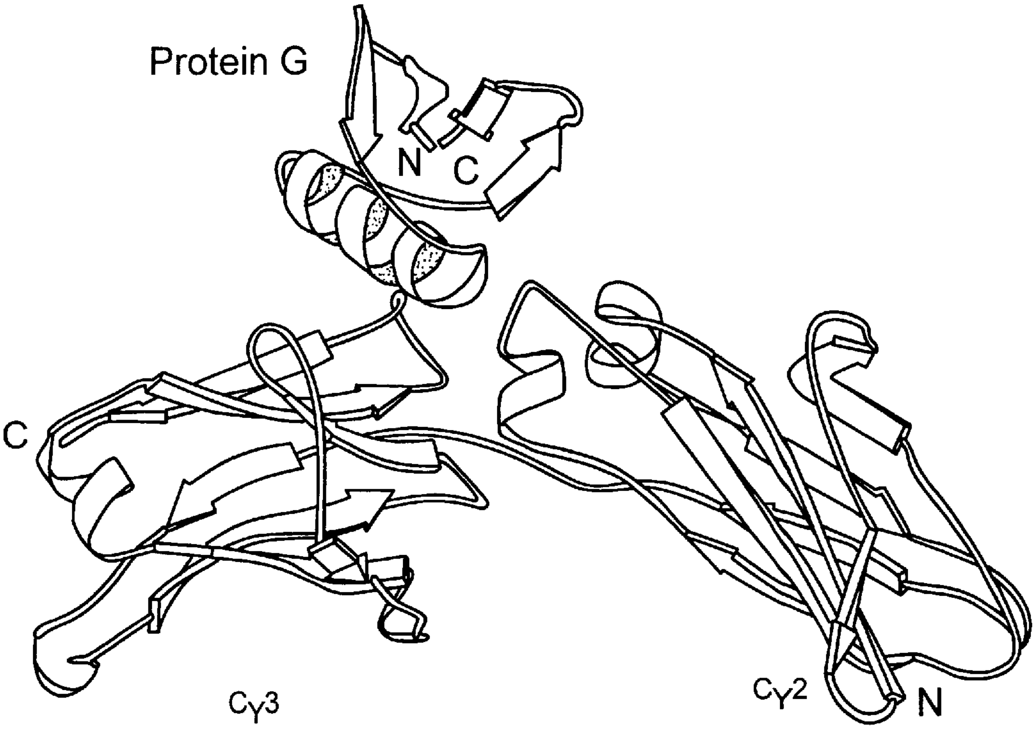

Streptococcal strains of serological groups C and G display a binding repertoire for mammalian IgGs, including human IgG3, which is even broader than for the type I receptor. The name protein G was suggested for this type III receptor from group G streptococci. In 1986 Olsson and co-workers reported on the cloning and sequencing of the gene from the serological group G streptococci [G148] [Guss, B. et al, 1987 EMBO J. 5:1567–1575; Olsson, A. et al, 1987 Eur.J.Biochem. 168:319–324]. In analogy with SPA is SPG a repetitively arranged molecule, comprising an IgG-binding region of three homologous domains [C1,C2, C3], spaced by smaller D-regions (FIG. 2A). Compared to SPA, SPG displays a different binding spectra for immunoglobulins from different species and subclasses thereof. The IgG binding domains of protein G are now widely used as an immunological tool, i.e. in the affinity purification of monoclonal antibodies. Production of subfragments constructed by DNA-technology, have shown that an individual C-region is sufficient for full IgG-binding. Recently, the structure for a complex between the C1-domain from SPG and human Fc was determined with X-ray crystallography (FIG. 2B). This shows that SPG binds to the CH2–CH3 interface but at a different site compared to SPA. The binding is mainly of electrostatic nature which is in contrast to the large contribution of hydrophobic forces seen for the SPA-Fc interaction. Moreover, the 3-D structure of C1 differs from the X structure in that it is built up by two β-sheets connected by an α-helix [ββ-α-ββ]. The residues of C1 which according to the structure are involved in the binding, corresponds to the α-helix, the loop and the following β-sheet.

An additional activity of SPG is the capability to bind serum albumin. The binding strength is species dependent, and among the tested samples. SPG binds strongest to serum albumin from rat, man and mouse. Production and binding studies of subfragments of SPG shows that the two binding activities are structurally separated and that the serum albumin binding function is located at the repetitive A-B region [Nygren et al 1990 Eur.J.Biochem. 193:143–148]. This region has been used for several biotechnological purposes. Recombinant proteins have been produced as fusions to the region which enables the purification by affinity chromatography, where human serum albumin most frequently has been used as immobilized ligand. Proteins found to be proteolytically sensitive have been produced as "dual affinity fusions" in which they are flanked by two different affinity tails derived from SPA and SPG, respectively. Purification schemes employing both the N- and C-terminal are thus possible which ensures the recovery of an intact target protein [Hammarberg et al 1989 Proc.Natl.Acad.Sciences USA 86:4367–4371]. The strong and specific binding to serum albumin has also been used for the in vivo stabilization of therapeutic proteins.

Through complex formation with the very long-lived serum albumin, the receptor is carried in the circulation (macque apes) with a half-life which is close to the half-life for serum albumin itself. Studies in mice with the for HIV/AIDS therapy interesting, but rapidly cleared T-cell receptor CD4, showed that it was substantially stabilized when fused to the serum albumin binding region, when compared with an unfused control protein [Nygren et al 1991 Vaccines 91 Cold Spring Harbor Press 363–368]. The slow clearance can probably be explained by the complex formation with serum albumin which circumvents elimination by the liver and excretion in the kidney.

In order to determine the minimal extension required for maintained binding to serum albumin, several smaller fragments of the A-B region have been produced and analyzed. The smallest fragment so far with serum albumin binding activity is a 46 residue fragment ["B2A3"] comprising region A3 flanked by 13 and 9 residues, respectively, from regions B2 and S.

Based on homology and binding studies of other partial fragments SPG is regarded to be trivalent with regard to binding to serum albumin. Similar to the monovalent IgG-binding domains Z and C1 B2A3 is relatively small and shows high solubility and stability and is therefore a suitable candidate for modification.

SUMMARY OF THE INVENTION

The present invention has for its main purpose to provide new bacterial receptor structures by modifying natural bacterial receptors in regard to their original interaction functions to result in new structures having modified interaction functions.

Another object of the invention is to provide artificial bacterial receptor structures which are stable and more resistant to various conditions, such as increased temperatures.

Yet another object of the invention is to provide artificial bacterial receptor structures, the interaction functions of which have been modified to direct same to other desired interaction partners.

With these and other objects that will be clear from the following disclosure in mind the invention provides for novel proteins obtainable by mutagenesis of surface-exposed amino acids of domains of natural bacterial receptors said proteins being obtained without substantial loss of basic structure and stability of said natural bacterial receptors. Said proteins have preferably been selected from a protein library embodying a repertoire of said novel proteins. In such novel bacterial receptor structures, at least one amino acid residue involved in the interaction fuction of the original bacterial receptor has been made subject to substitution by another amino acid residue so as to result in substantial loss of the original interaction capacity with a modified interaction capacity being created, said substitution being made without substantial loss of basic structure and stability of the original bacterial receptor.

It is preferred that said bacterial structures originate from Gram-positive bacteria. Among such bacteria there may be mentioned *Staphylococcus aureus, Streptococcus pyogenes* [group A], Streptococcus group C,G,L, bovine group G streptococci, *Streptococcus zooepidemicus* [group C], *Streptococcus zooepidemicus* S212, *Streptococcus pyogenes* [group A], streptococci groups A,C,G, *Peptostreptococcus magnus, Streptococcus agalactiae* [group B].

Of special interest are thermophilic bacteria evolved to persist in environments of elevated temperatures. Receptors from species like e.g. *Bacillus stearothermophilus, Thermus aquaticus, Thermococcus litoralis* and Pyrococcus have the potential of being naturally exceptionally stable, thus suitable for providing structural frameworks for protein engineering according to the invention.

It is particularly preferred to use as a starting material for the modification of the interaction function bacterial receptor structures originating from staphylococcal protein A or streptococcal protein G.

Among preferred receptors there may be mentioned bacterial receptors originating from Fc[IgG]receptor type I, type II, type III, type IV, type V and type VI, fibronectin receptor, M protein, plasmin receptor, collagen receptor, fibrinogen receptor or protein L [K light chains], protein H [human IgG], protein B [Human IgA,A1], protein Arp [human IgA].

Particularly preferred bacterial receptors originate from the Fc[IgG]receptor type I of staphylococcal protein A or the serum albumin receptor of streptococcal protein G.

In order to maintain stability and the properties of the original bacterial receptor structure it is preferred in accordance with the present invention that the substitution involving amino acid residues taking part in the interaction function of the original bacterial receptor does not involve more than about 50% of the amino acid residues of the original bacterial receptor. It is particularly preferred that not more than about 25% of the amino acid residues of the original bacterial receptor are made subject to substitution.

In regard to the original bacterial receptor structures selected from modification of their interaction functions it is particularly preferred to use receptors originating from the IgG-binding domains Z, Cl, and the serum albumin binding domains B2A3.

In order to maintain as far as possible the stability and properties of the original receptor structure subject to modification in accordance with the present invention it is preferred that substitution thereof involves not more than substantially all of the amino acid residues taking part in the interaction function of the original bacterial receptor.

In order to obtain favourable properties concerning stability and resistance to various conditions it is preferred that the bacterial receptor according to the present invention is comprised of not more than about 100 amino acid residues. It is known from scientific reports that proteins of a relatively small size are fairly resistant to increased temperatures and also to low pH and certain chemicals. For details concerning temperature resistance c.f. the article by Alexander et al. in Biochemistry 1992, 31, pp 3597–3603.

With regard to the modification of the natural bacterial receptor structure it is preferred to perform the substitution thereof by resorting to a genetic engineering, such as site-directed mutagenesis.

With regard to the interaction partner of the modified natural bacterial receptor a multitude of substances are conceivable, such as proteins, lipids, carbohydrates and inorganic substances. Among carbohydrates examples are blood group determinants and pathogen specific oligosaccharides.

In regard to proteins conceivable interaction partners are IGF-I, IGF-II, hGH, Factor VIII, insulin and apolipoprotein and their respective receptors as interaction partners. Furthermore, by selecting new receptor variants with specificity for different folding forms of proteins, affinity resins or analytical tools to facilitate the isolation of correctly folded molecules can be produced. Further examples are viral coat proteins, bacterial antigens, biotin and cell markers, such as CD 34 and CD 4.

Although the present invention is applicable to a variety of natural bacterial receptors the following illustration of the invention more in detail will be directed to the use of the IgG-binding domains Z, Cl and B2A3. The concept of the present invention residing in the use of artificial bacterial receptors based on the natural structures of naturally occurring bacterial receptors is associated with several advantages. Thus, the invention makes it possible to use robust and stable, highly soluble and secretion competent receptors. This is in contrast to previous techniques based on the use of polyclonals and monoclonals, such as for diagnostic purposes, which are not very stable in connection with storage, varying conditions, such as varying temperatures etc. Furthermore, the invention makes it possible to modify natural bacterial receptors to obtain desired interaction capacities for specific purposes.

For the selection of such functional variants in a large repertoire, a powerful selection system must be employed.

Recent developments in this field offer alternative methods. One of the most important tools for protein engineering that has emerged during the last years is the phage display of proteins. By recombinant DNA techniques, single phage particles can be prepared which on their surface carries a protein fused to a phage-coat protein. By panning from a large pool of phages bearing different proteins, or variants of a specific protein, specific phage clones can be sorted out, which displays a certain binding characteristic [WO92/20791 to Winter et al]. Since the phage particle contains packed DNA encoding the phage protein components, a coupling between the specific variant of the displayed protein and the corresponding genetic information is obtained. Using this technique, typically $10^9$ phage clones can simultaneously be generated and subjected to panning for screening of desired characteristics. The phage display technique can be used for selection of both small peptides as well as more complicated proteins such as antibodies, receptors and hormones. For selection of proteins which cannot be secreted, which is a prerequisite for phage display, intracellular systems have been developed in which the library of proteins are fused to a repressor protein with affinity for a specific plasmid-borne operator region resulting in a coupling between the specific protein variant and the plasmid that encoded it. An alternative to the phages as bearere of protein libraries be to use bacterial cells. Recently, display of recombinant proteins on the surface of *Staphylococcus xylosus* based on fusions to the cell-wall anchoring domain was demonstrated, which opens the possibility of display also of repertoires of proteins for affinity selection of specific variants [Hansson, M. et al 1992 J.Bacteriology 174:4239–4245]. Furthermore, by structure modelling using computer graphic simulations, predictions of the binding and function of altered variants of a protein can theoretically be done before the construction of the gene encoding the protein.

As indicated above the present invention describes the construction of novel proteins based on the mutagenesis of surface exposed amino acids of domains derived from bacterial receptors. These artificial bacterial receptors can be selected for different applications using a phage display system. The benefits from using bacterial receptors as structural frameworks are several. They have evolved to express a binding function without disturbing the overall structure. They are naturally highly soluble, robust to unphysiological conditions, such as pH and heat, folding efficient and are in addition secretion competent.

The invention finds use in several different areas.

The introductory part of the above-identified patent specification WO92/20791 gives an excellent survey on antibodies and their structure. Reference is particularly made to page 1 thereof.

The bacterial receptors SPA and SPG have been widely used in antibody technology for detection and purification of antibodies from e.g. hybridom supernatants and ascites fluids. However, not all antibodies are recognized by these receptors, depending on species and subclass. For the smaller subfragments of antibodies (FIG. 4), SPA and SPG show a limited binding, and efficient tools for general purification schemes are lacking. However, from a repertoire of mutant receptors including SPA and SPG, forms displaying a broader affinity for antibodies and subfragments thereof can potentially be selected.

The complex structural organization of antibodies has a number of consequences for their use in different applications as well for the production of recombinant derivatives. For use in immunosorbents, the arrangement of subunits connected by disulphide bonds can lead to a leakage of released heavy and light chains from columns. The requirement of successful docking of the two subunits contributing to the antigen binding site makes the production in bacteria of small subfragments with a low association difficult. The folding of the antibody is dependent on the formation of intra- and inter chain disulphidebonds, which are not able to form in the intracellular environment of bacterial cells. High-level intracellular expression systems for recombinant antibodies leads to the formation of inclusion bodies, which have to be renatured to obtain biological activity. These limitations make it worthwhile to search for alternatives for use as protein domains capable of specific binding, to replace antibodies in a vast number of applications.

The CDR regions forming the antigen bidning part of an antibody forms a total surface available for the antigen of approximately 800 Å$^2$, with typical 10–20 residues from the antibody involved in the binding. Using the structure of the complex determined by X-ray crystallography between an individual domain B of SPA and human fc[IgGI] as a starting point about 15 amino acids of the said domain involved in this binding can be determined or postulated. The binding surface of about 600 Å$^2$ is of the same order of magnitude as between an antibody and its antigen. By arbitrary in vitro mutagenesis of these positions simultaneously there is obtained a large library of Z variants with modified functional properties. In view of the fact that the regions of the Z domain constituting the very stabile so called three-helix bundle is maintained in its native form spectra of proteins are generated which could be considered as “artificial antibodies” and which have the expected high solubility and excellent folding properties capable of binding to a large number of new ligands. Fusions of these artificial receptors to constant regions can be constructed to recruite effector functions, such as complement binding or triggering of ADCC (antibody dependent cellular cytotoxicity).

There are several potential advantages of utilizing the SPA structure [Z] as a starting point for such “artificial antibodies” or artificial bacterial receptors. For a period of about 10 years a large number of proteins have been produced as fusions to SPA, where one has utilized the unique properties of the fusion partner in expression, refolding and purification. In these applications the Z domain has been found to be extremely soluble, stable against proteases, easy to produce in large amounts and foldable to a correct structure also intracellularly in *Escherichia coli* (no cysteins). Immunoglobulins (Ig:s) are substantially tetramers built up from so called β-sheet structures which stabilize the orientation of the antigen-binding loops which in turn consist of continuous peptide sequences. This is to be compared to the monomeric Z domain built up from so called three-helix bundle consisting of three closely packed α-helix structures, where the Fc-binding amino acids are found discontinuously in the sequence but in the folded protein are positioned on one and the same binding surface. This difference with regard to the structural elements contributing to the formation of the binding surface enables new possible conformations which cannot be obtained in natural antibodies. The ability of Z to be folded to the native structure also under conditions prevailing in the site of cytoplasma opens the possibility of using also derivatives thereof clinically. Genes coding for artificial antibodies with for example virus-neutralizing capacity can be distributed to cells through so called gene therapy resulting in interrupting the infection at an early stage.

From structure data for the complex between an individual Ig-binding domain [C1] of SPG and human Fc the binding surface can be studied. The binding which is essentially of an electrostatic nature involves side chains from amino acids from the α-helix as well as from the subsequent β-sheet [#3]. These differences in structure compared to the Z domain makes it useful also to create a library of C1 variants to investigate whether differences in binding patterns for artificial antibodies can be observed depending on the different conditions as regards the topology of the binding surface. Repertoires based on the structures of these and other receptors therefore offer different possibilities in the creation of artificial forms with novel functions.

When producing recombinant proteins the purification of the product is frequently a major problem. By expressing the target protein as a fusion to a so called affinity tail the hybrid product can effectively and selectively be recovered from the cell lysate or in certain cases from the culture medium by passage through a column containing an immobilized ligand. Several such gene fusion systems have been described which are based on the interaction of a certain protein with a ligand. For industrial applications it is often desirable to clean effectively the columns between the runs to satisfy purity requirements by authorities. Depending on the nature of proteins the relatively harsh conditions (NaOH, acids, heat) often used for organic or physical matrises, for example in ion exchange chromatography and gel filtration, can normally not be used. Here the use of new ligands based on stable structures originating from bacterial receptors are of great importance. In this connection the Z domain from SPA is an excellent example since said domain can be subjected to such difficult conditions as a pH of 1 or heating to 80° C. without denaturing non-reversibly (see Example 2 below). From the library of for example Z variants interesting protein products can be selected for use immobilized on a solid phase for affinity chromatography. These protein ligands are resistant to effective purification conditions and are therefore useful repetitively on a large scale. In traditional immuno affinity chromatography where immobilized monoclonal antibodies are used for the selective purification of a certain product there are problems with leakage from the column of subunits (heavy and light chains) of the antibody since it consists of four polypeptide chains linked by cystein bridges. Since the artificial bacterial receptors consist only of one polypeptide chain this problem will be avoided. One particular area of interest is selection for binding to carbohydrates. Lectins, nature's binders to this large and important group of biomolecules, have been found to be difficult to purify and have limited stability. Since the generation of antibodies against carbohydrates has been found to be quite complicated a selection of new artificial lectins will be of great importance to research, diagnostics and therapy.

In the production of recombinant proteins in bacterial hosts precipitates of the gene product are frequently formed, so called inclusion bodies. In order to obtain a native structure of the protein this must be subjected to refolding in vitro. A limitation in such process one is often confronted with is the fact that a great part of the material precipitates in the procedure which results in low yields. By producing the protein with an extension in the form of either a short hydrofilic peptide or an easily soluble complete domain [Samuelsson, E. et al 1991 Bio/Technol. 9:363–366] substantially higher concentrations of the protein will be obtained without precipitation taking place during renaturation. For example the high solubility of the said domain enables the use of increased solubility of proteins in either refolding from inclusion bodies or in so called reshuffling of disulphide bridges. From libraries of artificial receptors new forms can be selected having improved propeties to facilitate and even make refolding of recombinant proteins possible (cis-acting chaperones).

Recently a new unit operation for the purification of recombinant proteins based on ion exchange chromatography in so called expanded bed has been described (Hansson et al., 1994, Single-step recovery of a secreted recombinant protein by expanded bed adsorption, Biotechnol. (NY) 12: 285–288). In this connection there is used a difference in isoelectric point between the target protein and the proteins of the host cell for selective enrichment on a positively charged ion exchange matrix. By fusion to the acid Z domain (pI 4.7) the ion exchange step can take place at a pH, at which the majority of the contaminants were of the opposite charge compared to the fusion protein. By constructing libraries of bacterial receptors where a selection of amino acids have been replaced by the acid amino acids aspartate and glutamate also very acid and solubility increasing domains can be produced for use as fusion partners in the production of recombinant proteins.

As previously described affinity systems based on protein ligands are not totally suitable for industrial purposes in view of the harsh conditions required in the cleaning of columns. Therefore, there is a need for fusion partners having specific affinity towards simple and cheap organic ligands. Panning of phage display libraries of different bacterial receptors against such ligands provide novel affinity tails suitable for the use as fusion partners for the production purification of recombinant proteins.

The present invention provides means for producing and selecting proteins with novel functions. According to the invention this is achieved by extensive mutation of defined residues of stable domains of bacterial receptors. Due to the novel functions of the artificial bacterial receptors, these can be used as specific binders for therapeutic, diagnostic, biotechnology or in research.

Figure 1B:
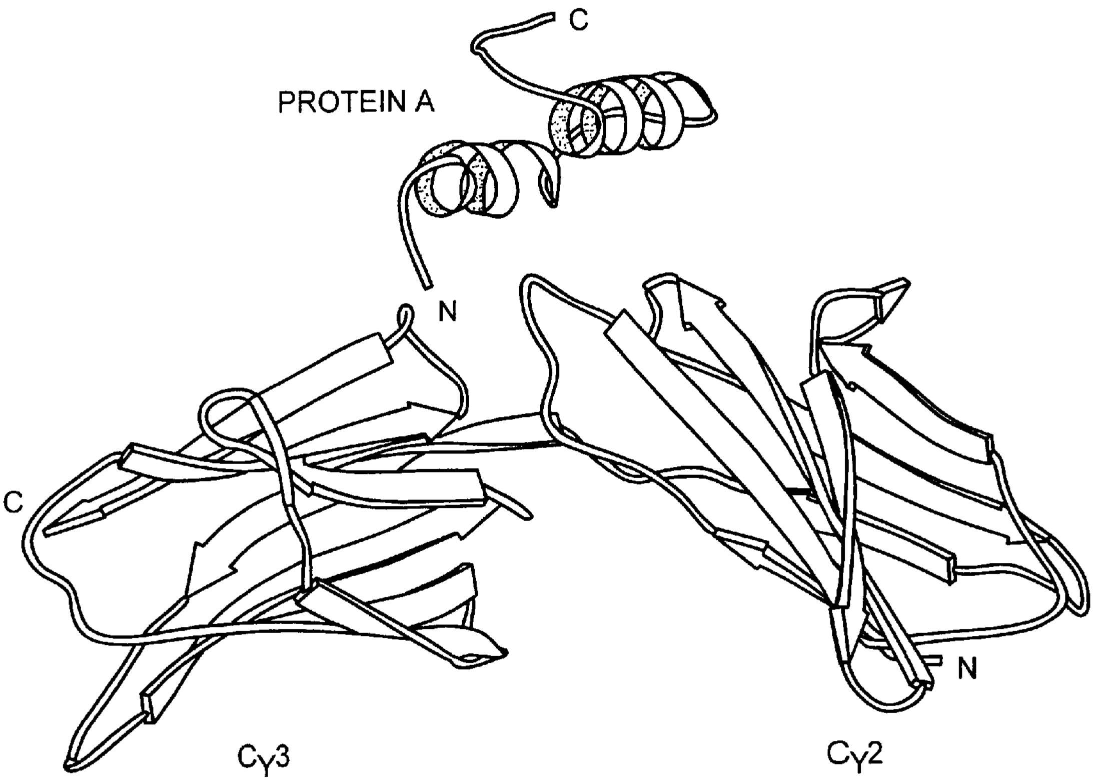

The present invention will now be described more in detail by specific examples with reference to the appended drawings. In the drawings:

FIG. 1. A. Schematic representation of staphylococcal protein A showing the signal peptide (S), five IgG-binding regions [E-D-A-B-C], followed by cell wall anchoring region [X-M]. B. Computer graphic representation of the complex between domain B from SPA and human Fcl determined by X-ray crystallography. Note that the third helix of SPA is not seen in this figure.

FIG. 2. A. Schematic representation of streptococcal protein G from the strain G148 showing the signal peptide (Ss), region E (E), the repetitive serum albumin binding A-B region, the spacer region (S), followed by the IgG binding domains C1 through C3, spaced by the D regions and finally the cell wall anchoring region W. B. Computer graphic representation of the complex between domain C1 of SPG and human Fcl determined by X-ray crystallography.

Figure 3:
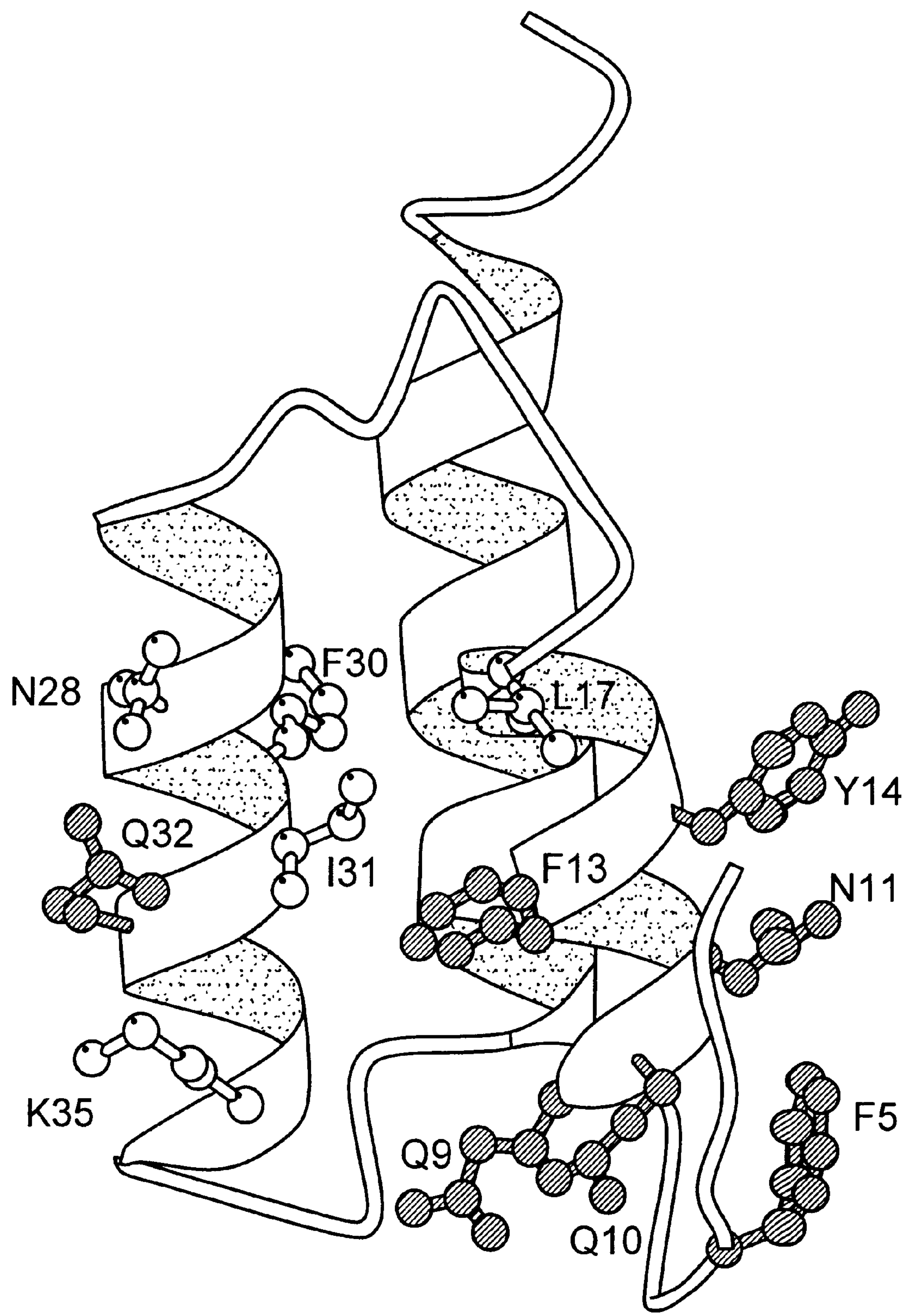

FIG. 3. Schematic representation of the three helix bundle structure of the 58 residue SPA analogue Z. Indicated are some of the side chains proposed to be involved in the binding to Fc with the exception of F30, which stabilizes the helix-helix packing.

Figure 4:
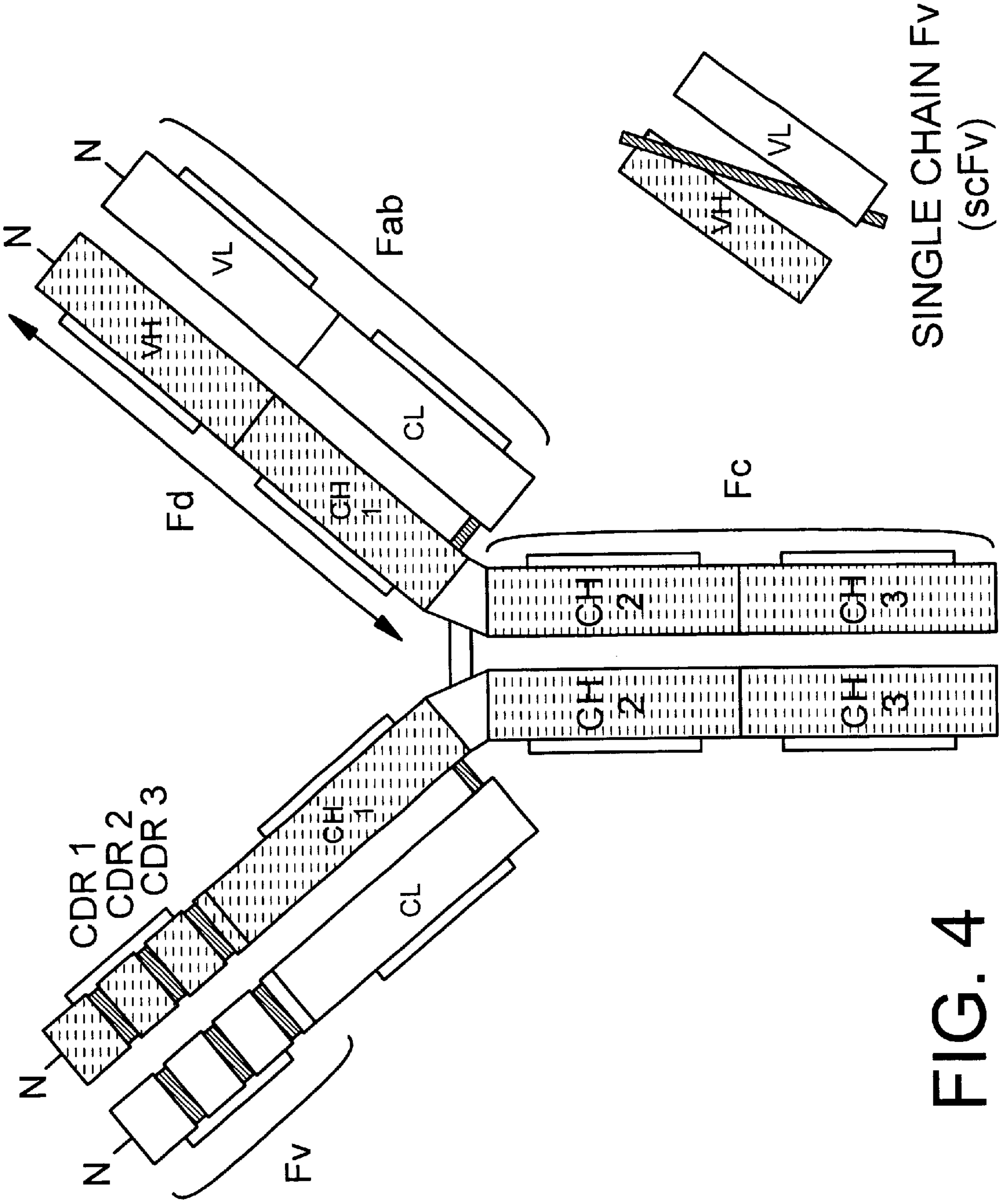

FIG. 4. IgG antibody structure, showing the different subfragments Fab,Fd,Fc and the scFv composed of the VH and VL connected by a short (ca 15 aa) linker.

FIG. 5.

A. General concept for the gene assembly strategy used for the generation of the Z gene libraries. For the construction of the library of acid Z derivatives, only residues 9, 11, 14, 27 and 35 were altered using the degenerated oligonucleotides ACID-1, ACID-2. The PCR primers used for the amplification of the assembled library were ZLIB-3 (PCR primer 5') and ZLIB-5 (PCR primer 3').

B. The PCR products from the amplification of the assembled library encoding 46 of the 58 residues of the Z-domain can be cloned into phagemid DNA harboring the remaining C-terminal part of Z. This gene is fused in frame with the gene for protein III of the M13 family of *E. coli* bacteriophages. This enables the display on the phage surface of the repertoire of acid Z-variants.

FIG. 6.

Oligonucleotides used for the construction of Z-libraries. For the library of acid Z-variants described in Example 2, only oligonucleotides ZLIB-1, 2, 3, 4, 5, LONGBRIDGE, ACID-1 and ACID-2 were used.

FIG. 7.

DNA sequences of clones derived from the acid Z protein library. Bold figures indicate amino acid positions in the Z-domain. For clarity the positions of the restriction sites Acc I and Nhe I are shown.

FIG. 8.

Result from analysis of the temperature stability of an individual Z domain at pH 2.9.The content of α-helicity in the sample was monitored by measuring the ellipticity at s222 nm during a temperature scan.

FIG. 9.

Phagemid vector pKN1. The library PCR products encoding the variegated helices 1 and 2 (both the acid and the extensive library) was subcloned into the phagemid vector, pKN1, containing the gene for residues 44–58 of the wild type Z domain (essentially helix 3), followed by the gene for a 46 residues serum albumin binding region (ABP) derived from streptococcal protein G linked in frame with a truncated version of the M13 phage coat protein 3 gene. The phagemid contains the origin of replication derived from plasmid pBR322 as well as the intergenic region (fl ori) required for packing into the phage particles.

FIG. 10.

SDS-PAGE. HSA-affinity purified proteins from the periplasm of *Escherichia coli* cells producing the wild type Z domain and two different acid Z-variants as ABP fusion proteins encoded from their respective phagemid vectors were analyzed by SDS/PAGE. M, molecular weight marker; lane 1, wild type Z domain; lane 2, clone 10; lane 3, clone 12.

FIG. 11.

CD-data. Overlay plot of CD spectra obtained for the wild type Z domain and two variants of the Z-protein library. The signals of the proteins were obtained after subtraction of the CD signal contribution of the ABP tail, present during the analysis.

FIG. 12.

Ion exchange chromatography. The two acid Z-variant proteins no. 10 and no. 12 together with the wild type Z-domain (produced as ABP fusion proteins) were each subjected to analysis at pH 5.5, employing an anion exchange chromatography column. Elution of the proteins from the column was obtained by a NaCl gradient. Top: acid Z-variant no. 12; middle, acid Z-variant no. 10; bottom, Z (wild type). Note that the wild type Z protein was not retarded on the column at this pH.

FIG. 13.

Z-domain structure. A main-chain trace representation of the model of the structure of the native Z-domain. The structure of helices one and two are from the co-crystal structure between domain B of SPA and Fc (Deisenhofer, (1981) Biochemistry, 20, 2361–2370). The third helix was built based on the secondary structure assignments from NMR specroscopy (Gouda et al., (1992) Biochemistry, 31, 9665–9672). Non-hydrogen atoms of side-chains of residues that were mutated in the construction of the combinatorial library are displayed as ball-and-stick models. The display was generated by the program MOLSCRIPT (Kraulis (1991) J.Appl. Cryst., 24, 946–950).

FIG. 14.

Amino acid sequences. Result from DNA-sequencing of 31 randomly chosen Z-variants from the library. The residues subjected to the mutagenesis are boxed. Horisontal lines indicate nucleotide identity with the wild type Z sequence listed at the top. Indicated are the clones that were expressed and characterized as fusion proteins to the ABP-tail.

FIG. 15.

Aminoacid distribution. Result from the statistical analysis of the deduced amino acids at the mutated positions. In total, 13 residues from 31 clones (403 codons) were included in the calculation. The ratios between observed and expected freuencies are shown for all 20 amino acids as well for the only termination signal (TAG) included in the NNG/T degeneracy profile.

FIG. 16.

SDS-PAGE analysis. HSA-affinity purified proteins from the periplasm of *E.coli* cells producing the wild type Z domain and four different Z-variants as ABP fusion proteins encoded from their respective phagemid vectors were analyzed by SDS/PAGE. Lanes 1–5: Reduced conditions. Lanes 6 and 7: Non-reduced conditions. Lane 1, wild type Z domain; lane 2, clone 16; lane 3, clone 21; lane 4, clone 22; lane 5, clone 24; M, molecular weight marker; lane 6, clone 16 and lane 7, clone 22.

FIG. 17.

CD-data. Overlay plot of CD spectra obtained for the wild type Z domain and four variants of the α-helical protein surface library. The signals of the variants were obtained after subtraction of the CD signal contribution of the ABP tail, present during the analysis.

FIG. 18.

Biosensor assay. An overlay plot of sensorgrams obtained from the BIA-core™ analysis of the wild type Z domain and four different variants (no. 16,21,22,24; FIG. 4) fused to the ABP tail. The IgG-binding activities of the different proteins were analyzed using a sensor chip coated with approx. 5000 RU human polyclonal IgG and injections of 45 μl pulses at 2 μl/min of 1500 nM solutions of the different proteins. Note that the differences in plateau values of signals during the injections of the variants no. 16,21,22 and 24 is due to divergent dilutions into the driving buffer.

All reagents and DNA constructions are available at the department for Biochemistry and Biotechnology, Royal Institute of Technology, Stockholm, Sweden.

Material

The oligonucleotides (FIG. 6) were purchased from Scandinavian Gene Synthesis (Sweden), and phosphorylated where indicated according to [Maniatis et al (1988) Molecular cloning. A laboratory manual. Cold Spring Harbor Laboratory Press]. ZLIB-1 was biotinylated in the 5'-end enabling immobilization on paramagnetic beads M-280 Streptavidin purchased from Dynal A/S (Norway). Washing/binding buffer was 1 M NaCl, 10 mM Tris-HCl, pH 7.5, 1 mM EDTA (ethylenediamine tetraacetic acid). The annealing/ligation buffer was 30 mM Tris-HCl, pH 7.5, 10 mM $MgCl_2$, 0.2 mM ATP, 1 mM 1.4 dithiothreitol (DTT). DNA ligase were from Boehringer Mannheim, Germany. 10×PCR buffer contained 20 mM $MgCl_2$, 2 mM dNTPs, 100 mM Tris-HCl, pH 8.3, 50 mM KCl, 1% Tween 20. Taq DNA polymerase was from Cetus Inc., USA. The thermal cycler was a Perkin-Elmer 9600. For the temperature/stability scanning a J-720 spectropolarimeter (JASCO, Japan) was used. *Escherichia coli* strain RR1ΔM15 [Rüther, U. (1982) Nucl.Acids Res. 10:5765–5772] prepared for competence [Maniatis et al. (1988) Molecular cloning. A laboratory manual. Cold Spring Harbor Laboratory Press] was used as host for the transformation. Agar plates contained 10 μg/ml of ampicillin.

EXAMPLE 1

Construction of an Acid Z-Library

Figure 5A:
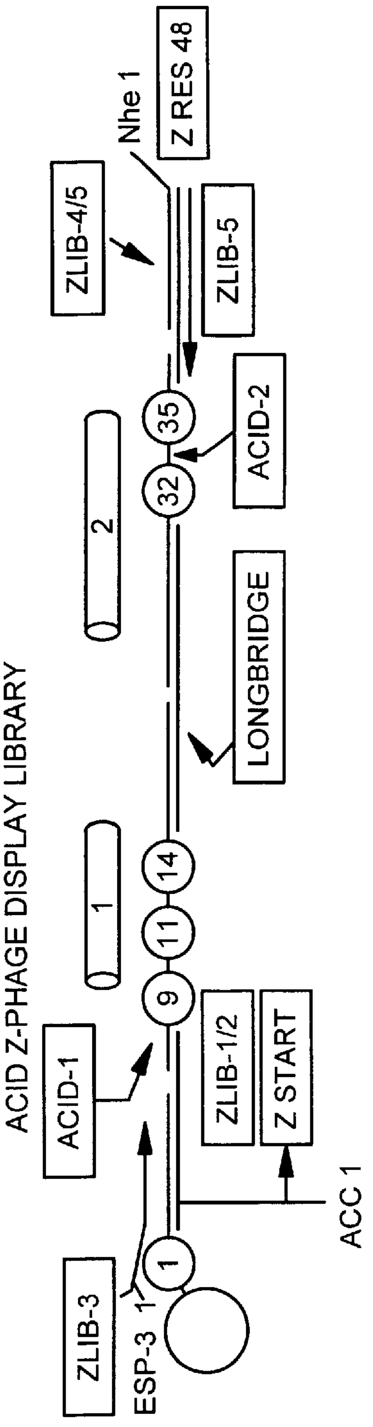
Figure 5B:
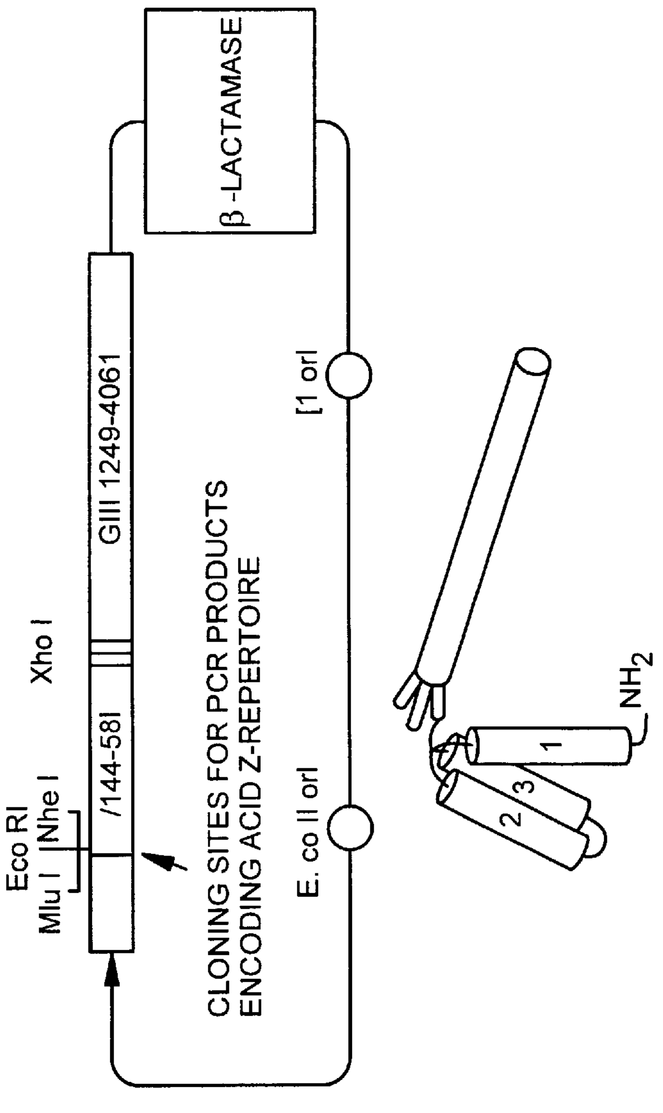
Figure 8:
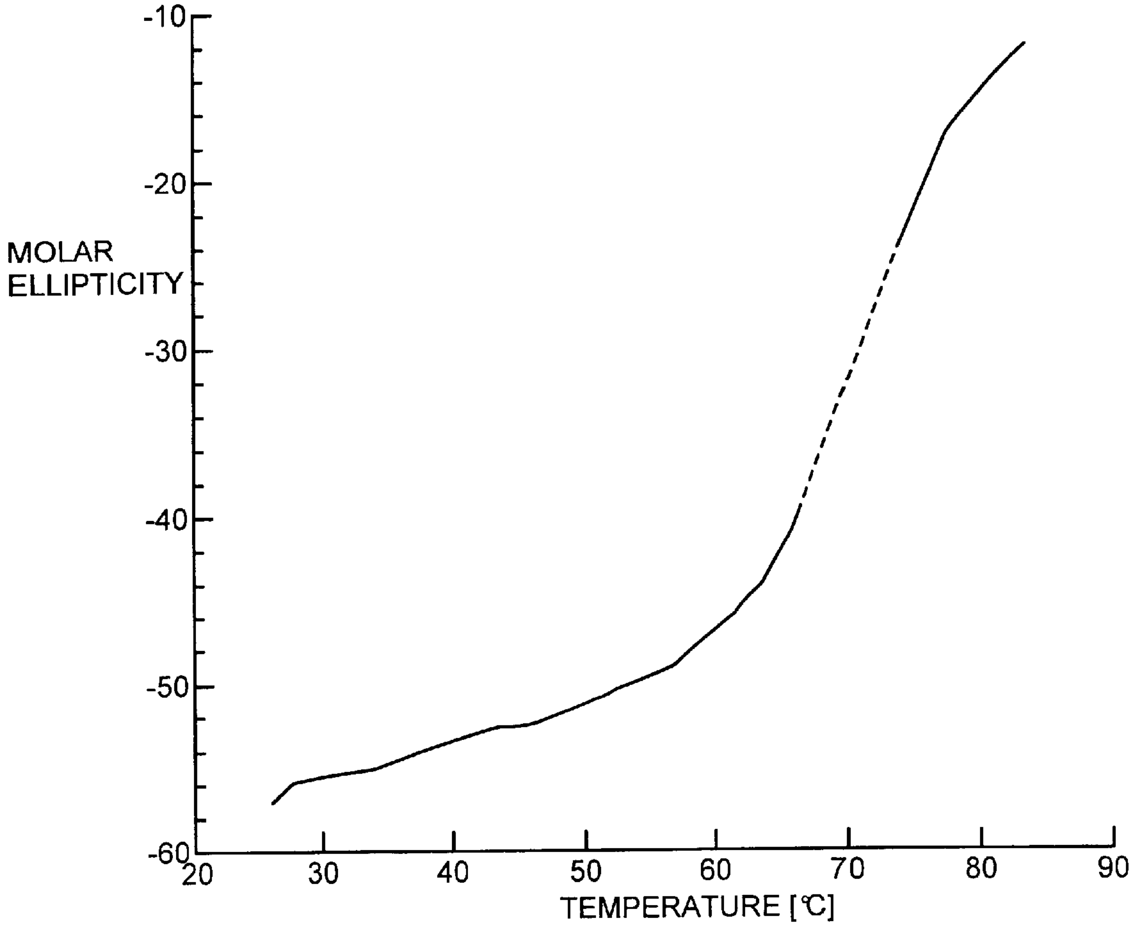

The synthetic 58 residue SPA analogue Z (Nilsson et al., 1987, A synthetic IgG-binding domain based on staphylococcal protein A, Protein Eng. 1:107–113) was subjected to a mutagenesis approach to construct new variants with an altered pI, in order to produce fusion partners for recombinant proteins to be purified by ion-exchange chromatography. Based on the crystal structure of the complex between the B-domain of SPA and human Fcl [Deisenhofer, J. et al 1981, Biochemistry 20:2361–2370], five residues from the B-domain participating in the binding were chosen as targets for mutagenesis. These five codons corresponding to the Z-residues No. 9, 11, 14, 27 and 35 positioned in helices 1 and 2 were altered simultaneously using degenerate oligonucleotides with the triplet sequence G(C/A)(C/A) at these positions resulting in the codons for the amino acids alanine (50%), aspartic acid (25%) and glutamic acid (25%), respectively. Using a solid phase gene assembly strategy [Ståhl et al, Biotechniques 14:424–434] a library of genes encoding $3^5$ (243) acidic variants of the synthetic IgG-binding Z-domain was created (FIG. 5). Twenty microliters (20 μg) of paramagnetic streptavidin-coated beads were washed with washing/binding buffer and incubated with 15 pmole of prehybridized oligonucleotides ZLIB-1 (biotinylated) and ZLIB-2, for 15 min at RT at a final volume of washing/binding buffer of 40 μl. After ligation and washing, approximately 15 pmole each of the oligonucleotides ACID-1 (degenerated), LONGBRIDGE, and ACID-2 (degenerated) and the preannealed linker pair ZLIB-4/ZLIB-5 were added in a repetitive manner, with intervening washing steps according to Ståhl et al [Biotechniques 14:424–434]. After completed assembly, the different fragments were ligated for 15 min at 37° C. To amplify the amount of DNA coding for the Z(Acid)-library still immobilized onto the beads, a fraction was withdrawn and subjected to PCR. The PCR mix (50 μl) contained one pmole each of PCR primers ZLIB-3 and ZLIB-5, 5 μl each of the ligation mix, 10×PCR buffer and 10×CHASE, 1 unit of Taq polymerase and sterile water to 50 μl. The temperature cycling programme was: 96° C., 1 min, 60° C., 1 min and 72° C., 2 min, repeated for 35 cycles. Analysis by 1% agarose gel electrophoresis showed a band of the expected size of 179 bp, showing the feasibility of the assembly concept. The 179 bp band from the PCR of the Z(Acid)-library, was cut out from the gel and purified (Geneclean™, Gio 101, Inc. USA) prior to insertion in a plasmid vector (TA-cloning™ kit, Invitrogen, Inc. USA) suitable for solid phase DNA sequencing [Hultman et al, 1988]. After transformation and spreading on ampicillin containing agar plates two colonies were chosen for analysis of the obtained sequences. The results (FIG. 6) show that the expected degeneracy was found at the desired positions.

EXAMPLE 2

Measurement of the Temperature Stability of the Z Conformation

The temperature stability of the Z conformation was determined by following the ellipticity at 222 nm by circular dichroism (CD) spectroscopy through a temperature scan. This wavelength is used to monitor the presence of α-helicity of Z [Cedergren et al. 1993 Prot. Eng. 6:441–448]. The experiment was performed at a rather low pH (approximately 2.9) in order to destabilize the molecule since the mid-point of temperature denaturation (Tm) is ≈95° C. at neutral pH (data not shown), which is outside the range that can be determined by a complete scan through the transition under normal atomspheric pressure. The experiment shows (FIG. 4) that the Tm (as defined by the inflexion point of the temperature scan) of the Z domain is as high as 71° C. at pH 2.9. This demonstrates the extreme temperature stability of the α-helices of the Z molecule.

The experiment was performed in a J-720 spectropolarimeter (JASCO, Japan) and the temperature was controlled by circulating water bath. The temperature was monitored in the cuvette through a micro sensor device (JASCO, Japan). The buffer was 50 mM acetic acid, pH 2.9. The protein was domain Z [Cedergren et al 1993 Prot. Eng. 6:441–448] at a protein concentration of 50 μg/mL and the cuvette cell path length was 1 cm. The temperature scan speed in the experiment was 50° C./h.

EXAMPLE 3

Characterization of Proteins Derived from the Acid Z-Library

Two protein variants derived from the acid Z-library were expressed in *Escherichia coli.* purified and characterized using SDS-PAGE, circular dichroism ion exchange chromatography. The PCR products from a solid phase gene assembly (see example 1) were restricted with 45 U Esp 3I (Labassco AB, Sweden) and 50 U Nhe I (Pharmacia, Sweden) in 200 μl buffer (33 mM Tris-acetate, pH 7.9, 10 mM Mg-acetate, 66 mM potassium-acetate, 0.5 mM DTT and 0.1 mg/ml BSA). The mix was overlaid with mineral oil and incubated at 37° C. over night. The restricted fragments (approximately 5 μg) were purified by phenol/chloroform/isoamylalcohol extraction followed by additional washing with chloroform and later ethanol precipitated before ligation at 15° C. over night to Mlu I-Nhe I cleaved pKN1 vector (1 μg) (see below) using 13.5 Weiss units of T4 DNA ligase. The ligation mixture was heat-treated at 70° C. for 20 min, extracted with phenol/chloroform/isoamylalcohol followed by washing with chloroform, ethanol precipitated and redissolved in 20 μl of sterile water.

The phagemid vector pKN1 (FIG. 9) was constructed in several steps as follows. A double stranded linker encoding the invariant residues 44–58 of the Z-domain was formed from oligonucleotides ZLIB-6 and ZLIB-7 and cloned as a Mlu I-Xho I fragment into phagemid pKP986 (A kind gift from Dr. Lars Abrahmsén, Pharmacia BioScience Center, Sweden), resulting in pKN. Plasmid pKP986 encodes the *E. coli* Omp A leader peptide followed by residues 249–406 of fd filamentous phage coat protein 3 (Lowman et al. (1991) *Biochemistry,* 30, 10832–10844.) under the control of a lac promoter. A gene fragment encoding a monovalent serum albumin binding region derived from streptococcal protein G was amplified by PCR from the plasmid pB2T (Eliasson et al., *Molecular Imunol.,* 28, 1055–1061), using primers ABP-1 and ABP-2 (which contains Xho I and Sal I recognition sites, respectively) and cloned into Xho I restricted plasmid pKN, yielding pKN1. This phagemid vector thus encodes for the Omp A signal peptide, the third helix of the wild type Z domain followed by a 46 residue albumin binding protein (ABP) linked to residues 249–406 of fd phage protein III and is adapted for insertion of Esp 3I/Hne I-digested PCR products encoding variegated helices one and two of the Z domain.

Freeze competent *E. coli* RR1ΔM15 (supE44 lacY1 lacZ ara-14 galK2 xyl-5 mil-1 leuB6 proA2 ΔimrcC-mrr) $recA^+$ rpsL20 thi-1 lambda-F[lac/ZΔM15]) (Rüther, 1982) *Nucleic Acids Research,* 10, 5765–5772) cells were transformed with the ligation mixture according to Maniatis and coworkers (Maniatis et al. (1982) *Molecular cloning: A Laboratory Manual*, Cold Spring Harbor, Cold Spring Harbon Laboratory Press) and plated on agar plates containing 100 μg/ml ampicillin (Sigma, USA) and 1% glucose. Small amount of cells from randomly picked colonies were separately subjected to two-step PCR amplifications (30 cycles: 96° C. 15 s; 72° C., 2 min) on a GeneAmp PCR System 9600 (Perkin Elmer, USA), using 5 pmoles of primers RIT-27 and NOKA-2 (biotinylated) in 20 mM TAPS (pH 9.3), 2 mM $MgCl_2$, 50 mM KCl, 0.1% Tween 20, 0.2 mM deoxyribonucleoside triphosphates (dNTPs), and 1.0 U of Taq DNA polymerase (Perkin-Elmer). The solid-phase DNA sequencing of the PCR products was performed employing the FITC labeled sequencing primers NOKA-3 (for the immobilized strand) and ABP-2 (for the eluted strand) on a robotic workstation (Biomek™ 1000, Beckman Instruments, Fullerton, Calif.) and an Automated Laser Fluorescent (A.L.F.) DNA Sequence™ (Pharmacia Biotech, Sweden) as described by Hultman and coworkers (Hultman et al., (1989) *Nucleic acids Research*, 17, 4937–4946).

Two clones with the different encoded acid aminoacid substitutions (bold face) at the positions 9, 11, 14, 27 and 35 in the Z-domian according to table 1 were selected for further analysis. The wild type Z domain and the two different acid Z-variant proteins (clones no. 10 and 12) were expressed from their respective phagemid vectors as fusions to the serum albumin binding tail (ABP) and purified by human serum albumin-affinity chromatography.

TABLE 1

Amino acid substitutions for selected clones in the acid Z-library[a].

| | Encoded aminio acid at position no. | | | | |
|---|---|---|---|---|---|
| Clone no. | 9 | 11 | 14 | 27 | 35 |
| w.t. | Gln | Asn | Tyr | Arg | Lys |
| 10 | Glu | Asp | Asp | Ala | Glu |
| 12 | Glu | Asp | Asp | Ala | Ala |

[a]Letters in bold face indicate acid aminacids

Figure 10:
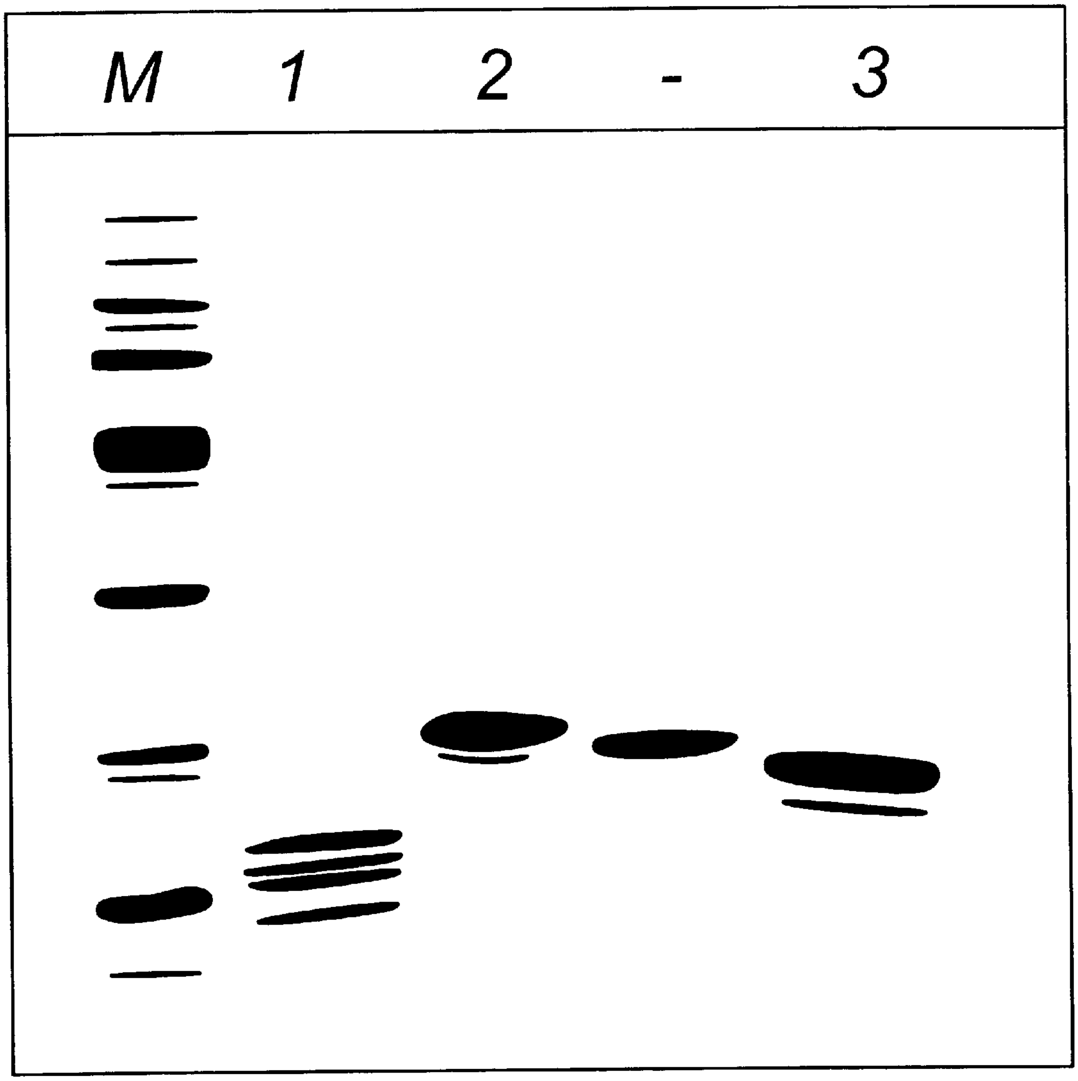

Colonies of *E. coli* RR1ΔM15 cells harbouring the corresponding phagemid vectors were used to inoculate 100 ml of Tryptic Soy Broth (Difco), supplemented with ampicillin (100 μg/ml). The cultures were grown at 37° C. to an $OD_{600\ nm}$=1, followed by induction with a final concentration of 1 mM IPTG and incubation at 30° C. over night. The cells were harvested by centrifugation at approximately 5000 g for 10 min and periplasmic proteins released by osmotic shock. The periplasmic content from the cells was subjected to affinity chromatography on HSA-Sepharose as described by Nygren and coworkers (Nygren, et al., (1988) *J. Mol Recognit.,* 1, 69–74) and analyzed by SDS/PAGE on a homogeneous 12% slab gel (BioRad Inc., USA), which was stained with Coomassie Brilliant Blue R-250. For all proteins appr. 1.5–2.5 mg/L culture could be recovered, indicating similar production and secretion efficiencies for the variants and the wild type domain. In addition, the results from the SDS-PAGE analysis (FIG. 10) of purified proteins suggest that the acid Z variants analyzed are stably expressed in *E. coli.*

To investigate if the secondary structure content of the derivatives was preserved after the surface mutagenesis, a subtractive circular dichroism analysis was performed. IgG- or HSA-affinity chromatography purified proteins Z, Z-ABP, the acid derivatives no. 10 and 12 fused to the ABP tail as well as the ABP-tail itself were subjected to a 250 to 184 nm (far UV) circular dichroism analysis at room temperature using a J-720 spectropolarimeter instrument (JASCO, Japan). The scanning speed was 10 nm/min. The cell pathlength was 1 mm. Solutions (approximately 0.1 mg/ml) of the different proteins were prepared n 20 mM phosphate buffer pH 6.5, supplemented with 0.05% Tween 20 (Kebo AB, Sweden). Accurate protein concentrations were determined by amino acid analysis on a Beckman 6300 amino acid analyzer equipped with System Gold data handling system. CD signals for the derivatives were obtained by subtracting the signal obtained for the ABP tail, after adjustments for differences in protein concentrations, followed by normalization for amino acid contents.

Figure 11:
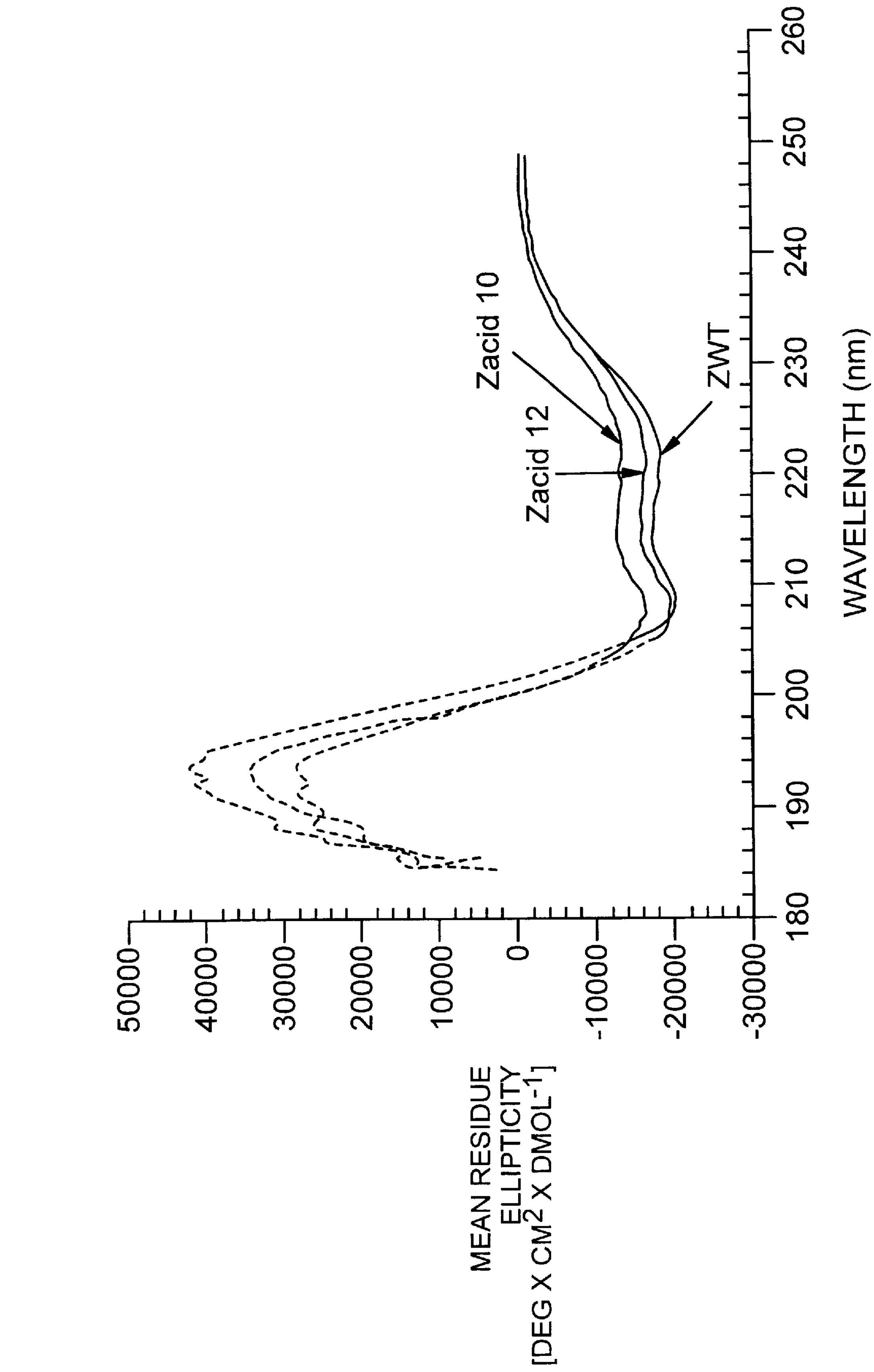

A comparison of signals obtained from 250 to 184 nm for the wild type Z domain and the acid variants fused to the ABP-tail was performed after subtraction of the contribution from the ABP tail itself. The result shows that for the two acid Z-derivatives, spectra similar to the wild type Z domain were obtained with a characteristic minimum at 208 nm and an inflexion point at 222 nm (Johnson, 1990) (FIG. 11). This suggests that the three helix bundle framework is preserved in these mutants.

Figure 12:
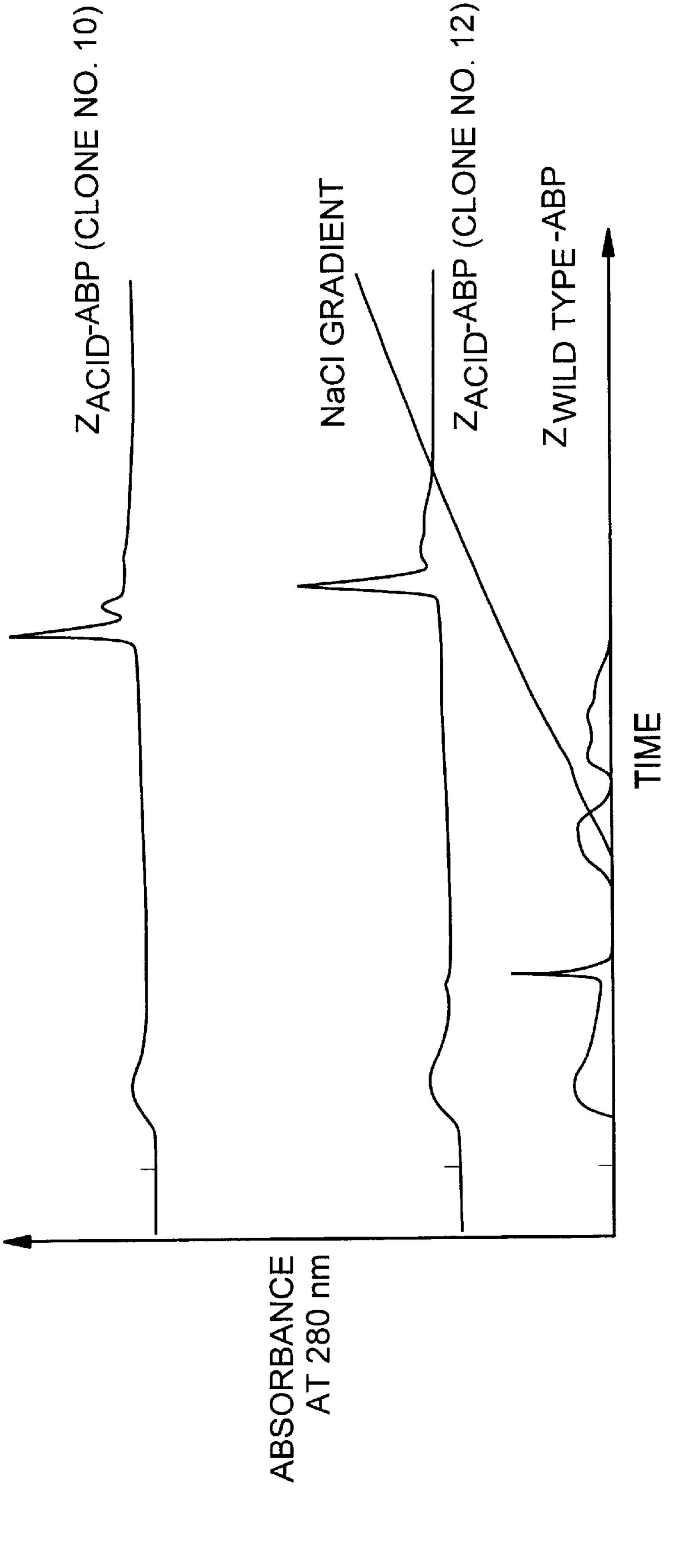

The two Z-variants, no. 10 and 12, contain four and three introduced acid aminoacids, respectively, compared to the native Z domain. In order to investigate if the introduced acidity was reflected as differences in their isoelectric points, they were subjected to a gradient elution from an anion exchange column. The proteins Z (wild type) and the acid variants no. 10 and no. 12 (all produced as ABP fusion proteins) were each (5 μg) dissolved in 300 μl of 20 mM Piperazine buffer (pH 5.5) and separately applied at 100 μl/min on a MonoQ. PC 1.6/5 column (Pharmacia, Sweden). Elution of the proteins were performed by applying a NaCl gradient in Piperazine buffer (pH 5.5) (Sigma, USA) ranging from 0–50% NacL in 20 min. The results from the analysis (FIG. 12) shows that the two acid Z.-variant proteins were eluted at different NaCl concentrations suggesting clear differences in isoelectric points. In contrast, at the pH chosen during the experiments, the wild type Z-domain did not interact with the resin, and was therefore seen in the flow-through.

Thus, the series of experiments performed on the two acid Z-variant proteins shows that the expression behaviour, proteolytic stability and secondary structure content of the variants were unchanged when compared to the native Z-domain. Furthermore, a novel functions were introduced into the two Z-variants by the substitution of surface located positions with acid amino acids. The two acid variants can be used e.g. as fusion partners to facilitate purification of recombinant proteins by ion exchange chromatography at low pH. Thus, it is showed that among the members of the acid Z-library, variants with novel functions can be isolated.

EXAMPLE 4

Construction and Characterization of a Combinatorial Library of Z-Variants

A library of Z-variants was assembled using a solid-phase gene assembly strategy (see example 1). Most of the amino acid residues suggested to take part in the binding to Fc (Diesenhofer, (1981) *Biochemistry,* 20, 2361–2370) were found to be on the molecule surface (Q9, Q10, N11, F13, Y14, L17, N28, Q32 and K35), and therefore included in the mutagenesis. In addition, based on their surfacial location, other residues (H18, E24, and R27) were also decided to be included. In total, 13 residues in the Z scaffold where thus chosen for simultaneous and random mutagenesis. A set of oligonucleotides (FIG. 6) were synthesized for construction of the library of surface mutants of the 58-residues monovalent IgG-bonding domain denoted A. In this library, the codons for Q9, Q10, N11, F13, Y14, L17 and H18 located in the first α-helix and E24, E25, R27, N28, Q32 and K35 in the second α-helix of the Z domain (FIG. 13) were substituted for degenerate NNK (K=G or T) codons using a solid phase strategy utilizing the single stranded degenerate oligonucleotides for the assembly. The chosen NNK degeneracy includes 32 codons covering all 20 amino acids, including the TAG (amber) termination signal.

Oligonucleotide ZLIB-1 was synthesized with a 5' biotin group to enable robust anchoring onto streptavidin-coated paramagnetic beads used as solid support during the gene assembly. This ZLIB-1 oligonucleotide, together with its complementary sequence (ZLIB-2) encodes residues 1–8 of the Z domain, preceeded by the first six residues of region E of protein A which were included to facilitate the *E. coli* secretion of the Z variants (Abrahmsén et al., (1986) *EMBO J.,* 4, 3901–3906). The oligonucleotides DEGEN-1 and DEGEN-2 (Table I) encode the two mutated helices of the Z domain, respectively, normally involved in Fc-binding. Theoretically, full and simultaneous NNK degeneracy at the 13 selected positions would yield a combinatorial library of appr. $8 \cdot 10^{16}$ protein variants encoded by $3.7 \cdot 10^{19}$ different DNA sequences. However, here the assembly of the library was initiated by the immobilization of appr. 15 pmole of prehybridized oligonucleotides ZLIB-1 and ZLIB-2 (FIG. 6), which limits the theoretical size of the Z-library to appr. $0.9 \cdot 10^{13}$ different DNA sequences encoding appr. $2 \cdot 10^{10}$ Z variants. The assembly was continued by the addition and ligation of a preformed construct, obtained after ligation of equimolar amounts of oligonucleotides DEGEN-1 and DEGEN-2, facilitated by the bridging oligonucleotide BRIDGE (FIG. 6).

To complete the assembly, a fragment consisting of the prehybridized oligonucleotides ZLIB-4 and ZLIB-5 was added to the beads for ligation. This fragment encodes the second loop and the first six residues of the unaltered third helix of the Z domain. After completed assembly, oligonucleotides ZLIB-3 and ZLIB-5, containing the recognition sequences for the endonucleotides ZLIB-3 and ZLIB-5, containing the recognition sequences for the endonucleases Esp 3 I and Nhe I respectively, were used as primers for PCR amplification of the assembled constructs using one tenth of the bead-immobilized ssDNA as template (theoretically corresponding to $2 \cdot 10^{9}$ protein variants). To avoid unwanted interference during the amplification, oligonucleotides ZLIB-2, BRIDGE and ZLIB-5 were first eluted with alkali. The resulting PCR product was analysed by agarose gel electrophoresis and found to be homogenous and of the expected size, 179 bp.

Figure 9:
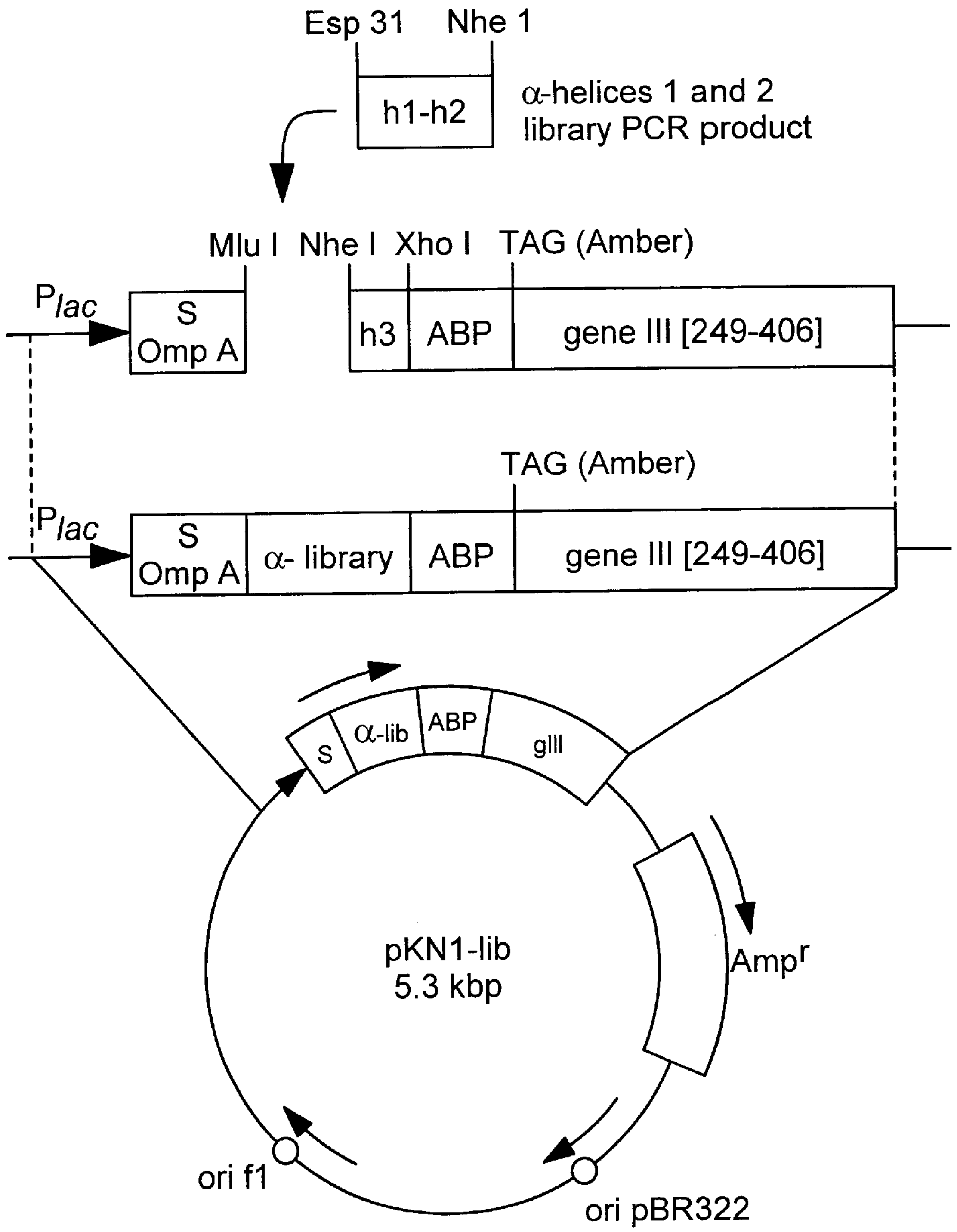

The PCR product was subcloned into the pKN1 phagemid vector containing the gene for residues 44–58 of the wild type Z domain in frame with a truncated version of the fd phage coat protein 3 gene for surface display on phage particles upon helper phage superinfection of phagemid transformed *E. coli* cells (Lowman et al., (1991) *Biochemistry,* 30, 10832–10844) (FIG. 9). In addition, the phagemid vector contains an interspaced in-frame cassette encoding a 5 kDa (46 aa) serum albumin binding region (denoted ABP) derived from streptococcal protein G (Nygren et al., (1988) *J. Mol. Recognit.,* 1, 69–74; Nilsson et al., (1994) *Eur. J. Biochem.,* 224, 103–108), enabling efficient affinity purification of produced Z variants devoid of their native Fe-binding activity. Furthermore, the serum albumin binding activity can potentially be used for preselection of phage particles carrying recombinant molecules, prior to the panning for Z variants with new binding functions, to decrease the background originating from unspecifically bound non-recombinant phase particles.

Figure 13:
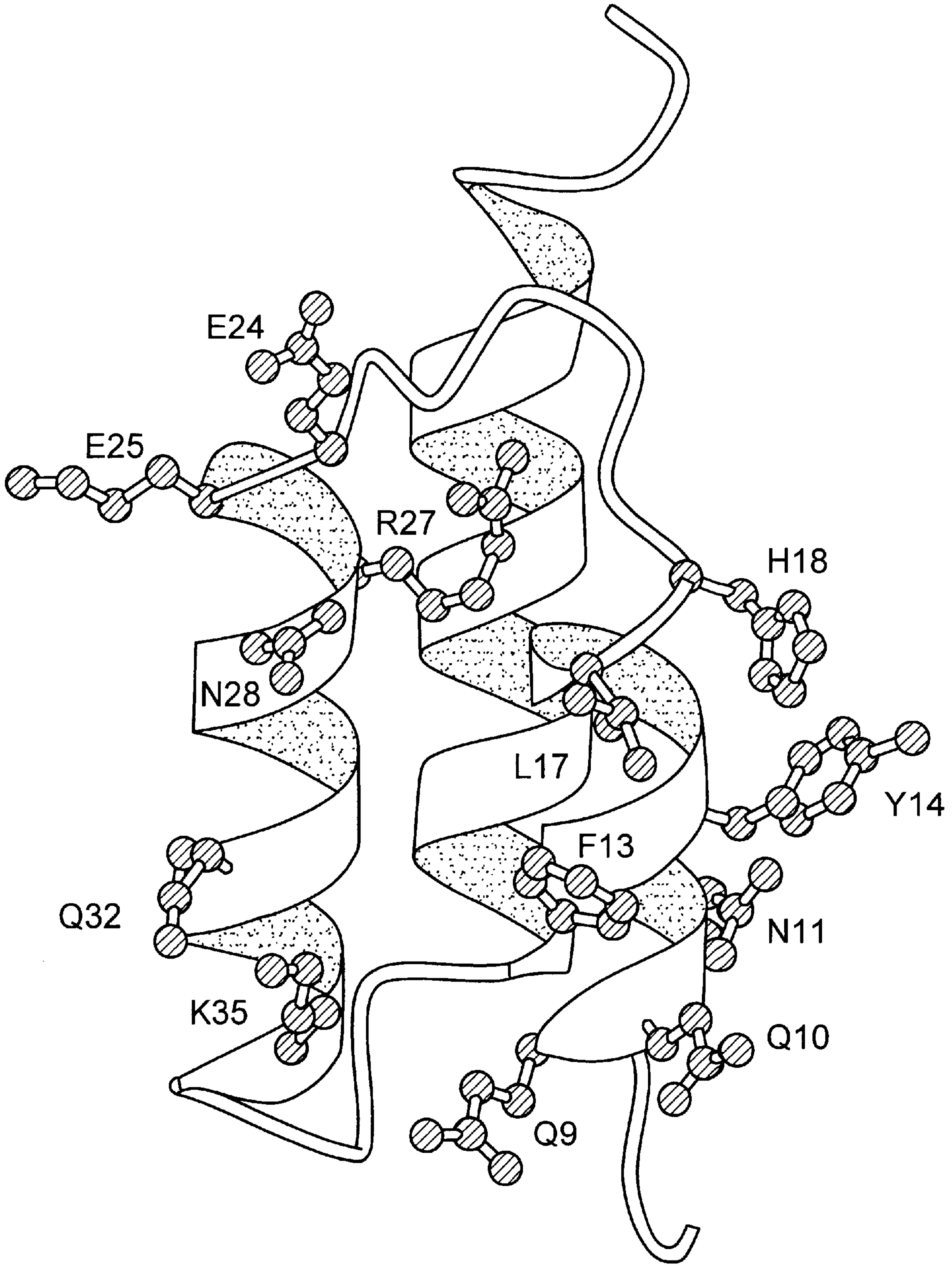
Figure 14B:
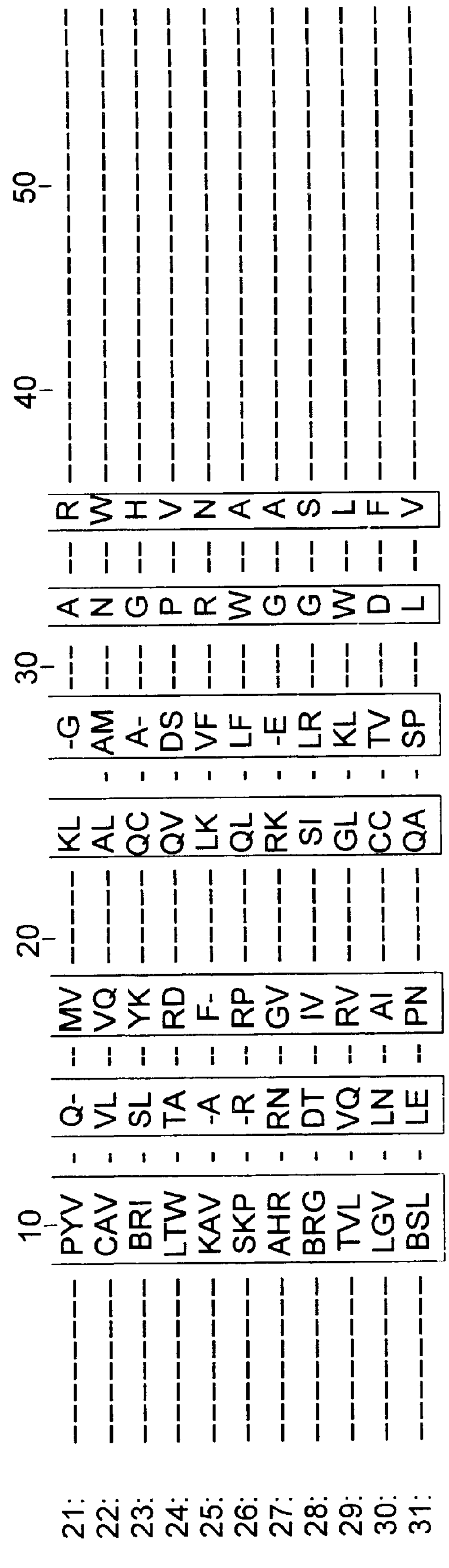
Figure 15:
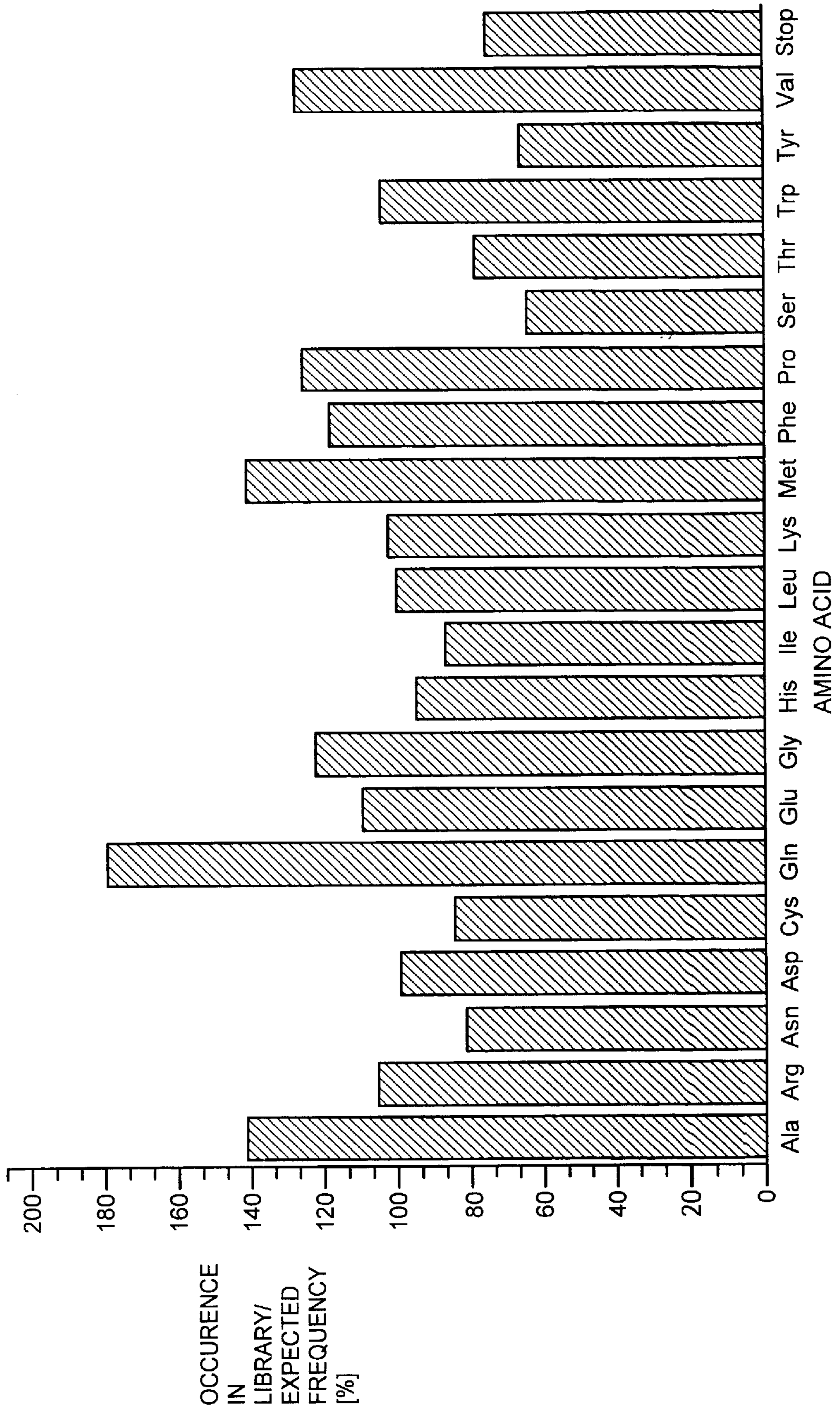
Figure 16:
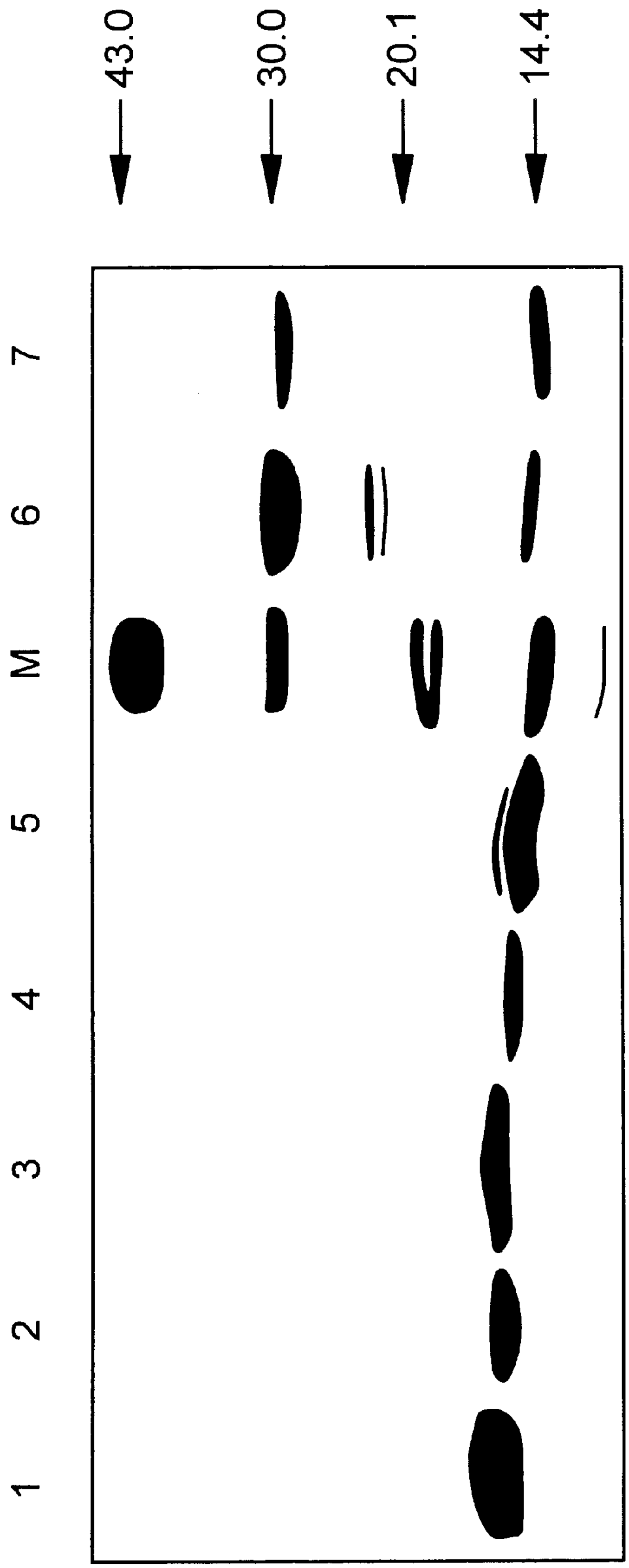

After transformation, PCR screening (using the oligonucleotides RIT-27 and NOKA-2) of 25 clones showed that over 95% (24/25) of the clones contained an insert of the expected length, suggesting that the gene assembly procedure was carried out with high efficiency. Fortyfive transformants were randomly selected and subjected to direct solid phase DNA sequencing (see Example 3) in order to further analyze the quality and heterogeneity of the library. Approximately 69% of the clones were correct, containing wild type and degenerate codons at expected positions. The remaining clones had spurious discrepancies which in part can be attributed to the oligonucleotide synthesis or errors introduced during PCR. The correct clones (31 clones) (FIG. 14) were further analyzed for codon representation at the 13 degenerate positions. The distribution of the total 403 resulting deduced amino acids among the 32 codons included in the NNK degeneracy profile shows a close correlation with the expected frequencies for these yet unselected clones (FIG. 15). To investigate the expression and stability of the Z-variants, four clones (no. 16, 21, 22, 24; FIG. 14) with different degrees of substitution as well as the wild type Z domain were produced as ABP fusions encoded from their respective phagemid vectors. Soluble proteins from the periplasm of IPTG-induced cultures were subjected to HSA-affinity chromatography employing the ABP-tail for general and efficient recovery (Nygren et al., (1988) *J. Mol. Recognit.,* 1, 69–74). For all proteins appr. 1.5–2.5 mg/L culture could be recovered, indicating similar production and secretion efficiencies for the variants and the wild type domain. The results from a SDS-PAGE analysis (FIG. 16) of purified proteins suggest that the four Z variants-analyzed are stably expressed in *E. coli.* The smaller band with HSA-binding activity, seen with different intensities most probably corresponds to the ABP-tail itself (5 kDa), resulting from proteolytic cleavage between the Z variant and the ABP tail. Interestingly, both Z-variants (no. 16 and 22) with introduced cysteine residues formed dimers, which could be observed under non-reducing conditions during SDS-PAGE (FIG. 13; lanes 6 and 7).

Figure 17:
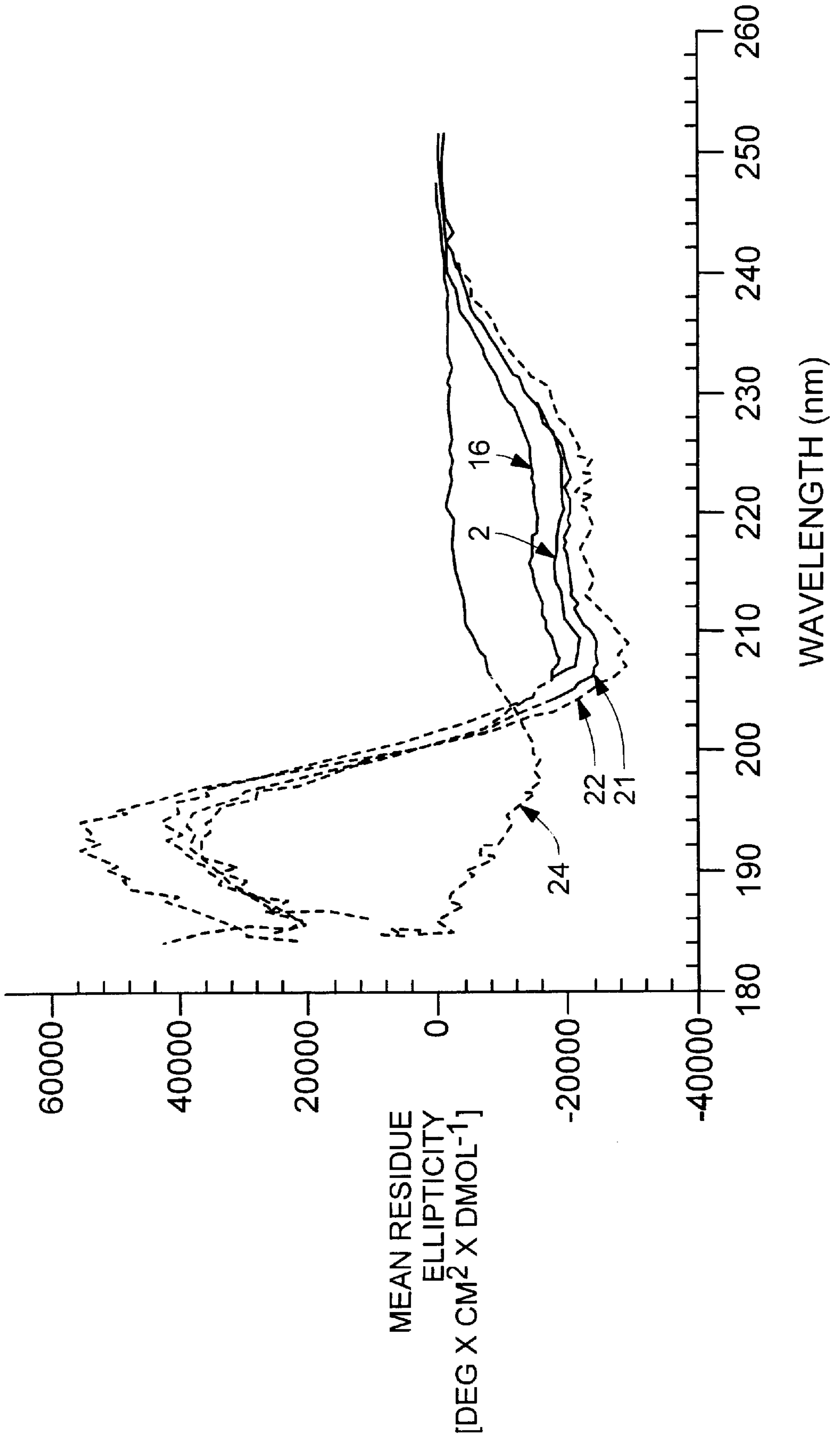

To investigate if the secondary structure content of the derivatives was preserved after the extensive surface mutagenesis, a subtractive circular dichroism analysis was performed (see example 3). A comparison of signals obtained from 250 to 184 nm for the wild type Z domain and the four variants fused to the ABP-tail was performed after subtraction of the contribution from the ABP tail itself. The result showed that for three of the four derivatives spectra similar to the wild type Z domain were obtained, with a characteristic minimum at 208 nm and an inflexion point at 22 nm (Johnson, (1990) *Prot. Struct. Funct., Genet.,* 7, 205–224) (FIG. 17). This suggests that the three helix bundle framework probably is preserved in these mutants. However, for the fourth derivative (no. 24), a spectrum was obtained which resembles spectra seen for random coils, indicating a low content of secondary structure elements (Johnson, 1990). This derivative contains a glutamine to proline substitution at position 32 in helix 2, suggesting a destabilization leading to a collapse of the helix bundle framework.

Figure 18:
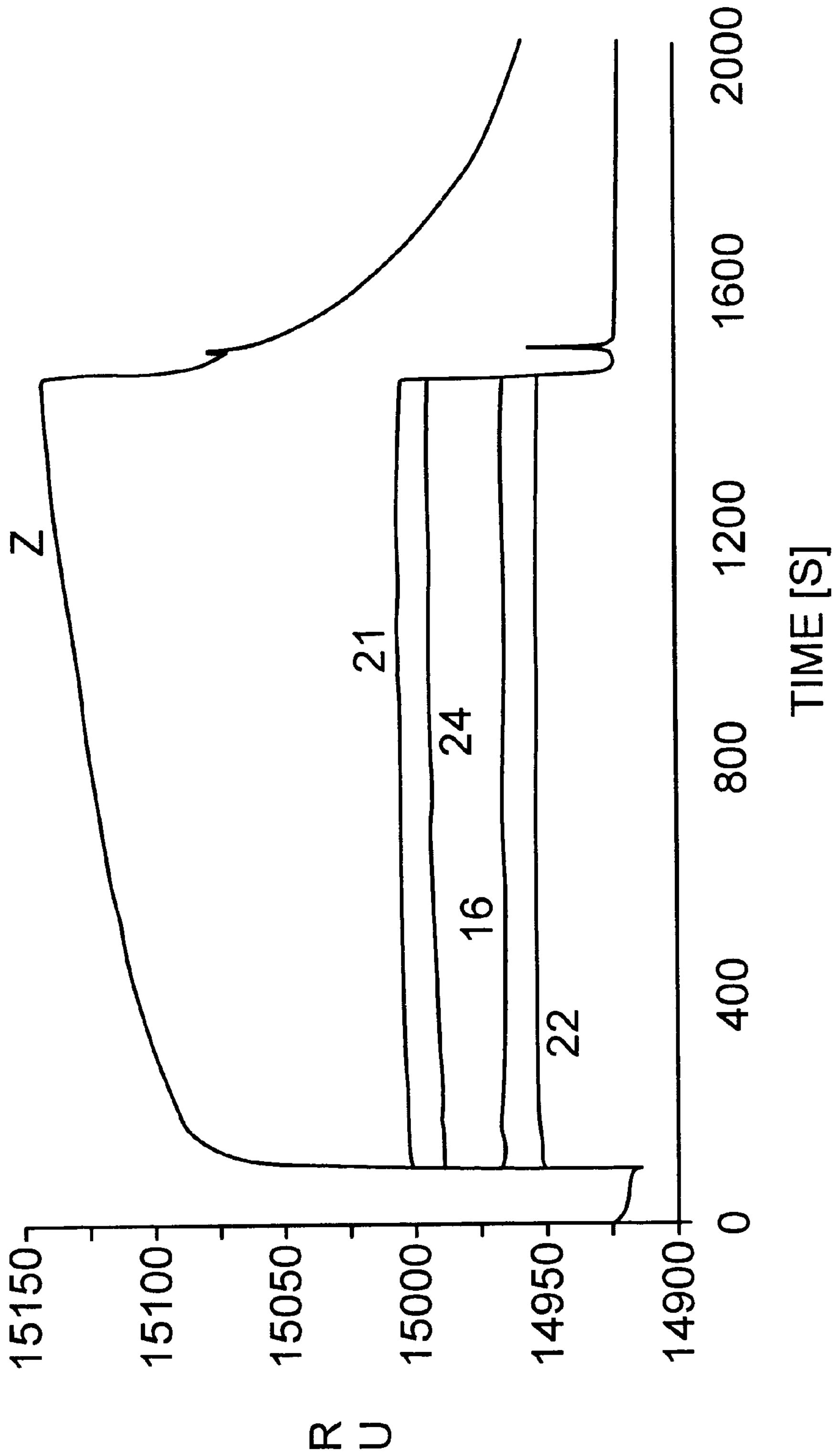

In order to further investigate the four Z-variants, the interaction with polyclonal human IgG (hIgG) (Pharmacia AB) for wile type Z and four different Z variant clones (no. 16, 21, 22, 24; FIG. 14) fused to the ABP tail were compared using biosensor technology (BIAcore™, Pharmacia Biosensor AB, Sweden). The carboxylated dextran layer of a CM-5 sensor chip was activated using N-hydroxysuccinimide (NHS) and N-ethyl-N'-[3-diethylaminopropyl]-carbodiimide (EDC) chemistry according to the manufacturers' recommendations. For immobilization of hIgG, 20 $\mu$l of a 500 mM hIgG solution in 50 mM acetate, pH 4 was injected at a flow rate of 5 $\mu$l/min over the activated surface, resulting in the immobilization of approximately 5000 resonance units (RU). Fortyfive-microliter samples of the five fusion proteins, dissolved to approximate concentrations of 1500 nM in NaCl/Hepes (10 mM Hepes, pH 7.4, 150 mM NaCl, 3.4 mM EDTA, 0.5% surfactant P-20), were injected in separate experiments at a flow rate of 2 $\mu$l/min. After each sample injection, the hIgG surface was regenerated with 20 mM HCl. As expected, only the wild type Z-domain showed any detectable Fe-binding activity (FIG. 18).

In conclusion, the results show that a library of SPA variants with a substituted surface made up from 13 residues located in the α-helices can be constructed. The high degree of conservation of the overall framework of the native Z-domain suggests that derivatives with novel functions grafted onto a stable and soluble scaffold could be isolated for use as artificial antibodies in biochemistry, immunology and biotechology.

What is claimed is:

1. Novel proteins comprising one or more mutations of surface-exposed amino acids of domains of natural bacterial receptors, said one or more mutations resulting in modification of the natural bacterial receptors in regard to their original interaction functions to direct them to different binding partners, and said modification resulting in artificial bacterial structures wherein the basic structure and stability of said natural bacterial receptors is not lost.

2. Proteins according to claim 1, which are fused to a phage-coat protein.

3. Proteins according to claim 2, wherein said natural bacterial receptors originate from bacteria selected from *Staphylococcus aureus, Streptococcus pyogenes* (group A), Streptococcus groups C,G,L, bovine group G streptococci, *Streptococcus zooepidemicus* (group C), *Streptococcus zooepidemicus* S212, streptococci groups A,C,G, *Peptostreptococcus magnus, Streptococcus agalactiae* (group B).

4. Proteins according to claim 3, wherein said natural bacterial receptors originate from staphylococcal protein A or streptococcal protein G.

5. Proteins according to claim 3, wherein said natural bacterial receptors originate from receptors selected from Fe receptor IgG type I, type II, type III, type IV, type V and type VI, fibronectin receptor, M protein, plasmin receptor, collagen receptor, fibrinogen receptor or protein L (K light chains), protein H (human IgG), protein B (human IgG, Al), protein Arp (human IgA).

6. Proteins according to claim 4, wherein said receptor originates from the Fc receptor IgG type I of staphylococcal protein A or the serum albumin receptor of streptococcal protein G.

7. Proteins according to claim 6, wherein said receptor originates from the IgG-binding domains Z, Cl, and the serum albumin binding domain B2A3.

8. Proteins according to claim 1, wherein said modification involves at most about 50% of the amino acid residues of the natural bacterial receptor.

9. Proteins according to claim 8, wherein said modification involves at most about 25% of the amino acid residues of the natural bacterial receptor.

10. Proteins according to claim 1, wherein said modification involves not more than all of the amino acid residues taking part in the interaction function(s) of the natural bacterial receptor.

11. Proteins according to claim 1, wherein said modification has been obtained by site-directed mutagenesis.

12. Proteins according to claim 1, wherein said modification is directed to creating specific interaction capacity vis-à-vis substances selected from proteins, lipids, carbohydrates and inorganic substances as interaction partners.

13. Proteins according to claim 12, wherein said substances are carbohydrates.

14. Proteins according to claim 12, wherein said substances are selected from IGF-I, IGF-II, hGH, Factor VIII, insulin and apolipoprotein and their respective receptors as interaction partners.

15. Proteins according to claim 12, wherein said modification is directed to creating specific interaction capacity vis-à-vis substance selected from viral coat proteins, bacterial antigens, biotin, and cell markers.

16. Proteins according to claim 12, wherein said modification is directed to creating specific interaction capacity vis-à-vis antibody fragments.

17. Proteins according to claim 12, wherein said modification is directed to creating specific interaction capacity vis-à-vis organic ligands.

18. Proteins according to claim 1, which have been selected from a protein library embodying a repertoire of said novel proteins.

19. A method for the manufacture of an artificial bacterial receptor structure comprising the steps:

a) subjecting a repertoire of novel receptor structures obtained according to claim 1 to a selection procedure based on a desired interaction function; and b) isolating the selected receptor structure.

20. A method according to claim 19, comprising the steps:

a1) preparing, by recombinant DNA techniques, phage particles carrying on their respective surfaces proteins from said repertoire of novel receptor structures and fused to phage-coat proteins;

a2) panning from a pool of phage particles resulting from step a1) to select specific phage clones displaying desired binding characteristics; and b) isolating said specific phage clones using interactions associated with said binding characteristics.

21. A method according to claim 19 for selection of receptor structures associated with protein of a non-secretory nature, comprising the steps:

a) preparing, by recombinant DNA techniques, fusion proteins, wherein the proteins of said library are fused to a repressor protein with affinity for a specific plasmid-borne operator region resulting in interaction between a specific protein variant and a plasmid encoding the same; and b) isolating selected proteins using said interaction.

22. A method according to claim 19, comprising the steps:

a1) preparing, by recombinant DNA techniques, bacterial cells carrying on their respective surfaces proteins from said repertoire of novel receptor structures and fused to cell-wall anchoring domains functional in said bacterial cells;

a2) panning from a pool of bacterial cells resulting from step a1) to select specific bacterial clones displaying desired binding characteristics; and b) isolating said specific clones using interactions associated with said binding characteristics.

23. Proteins according to claim 3, wherein said bacterial receptors originate from receptors selected from Fc receptor IgG type I, type II, type III, type IV, type V and type VI, fibronectin receptor, M protein, plasmin receptor, collagen receptor, fibrinogen receptor or protein L (K light chains), protein H (human IgG), protein B (human IgA, Al), protein Arp (human IgA).

24. Proteins according to claim 2, wherein said bacterial receptors originate from Gram-positive bacteria.

25. Proteins according to claim 13, wherein said carbohydrates are selected from the group consisting of blood group determinants and pathogen-specific oligosaccharides.

26. Proteins according to claim 15, wherein said cell markers are selected from the group consisting of CD34 and CD4.

27. Proteins according to claim 16, wherein said antibody fragments are selected from the group consisting of Fv, scFv, Fab, and Fc fragments.

28. A protein comprising an artificial bacterial receptor structure, wherein the amino acid sequence of the artificial bacterial receptor structure corresponds to that of a natural bacterial receptor having at least one surface-exposed amino acid residue substituted by another amino acid residue, wherein the basic structure and stability of the natural bacterial receptor is not lost, wherein the artificial bacterial receptor structure lacks an interaction capacity of the natural bacterial receptor, and wherein the artificial bacterial receptor structure binds to an interaction partner to which the natural bacterial receptor does not bind.

29. The protein of claim 28, further comprising a phage-coat protein.

30. The protein of claim 29, wherein the natural bacterial receptor is a receptor in a bacterial species selected from the group consisting of *Staphylococcus aureus, Streptococcus pyogenes* (group A), Streptococcus groups C,G,L, bovine group G streptococci, *Streptococcus zooepidemicus* (group C), *Streptococcus zooepidemicus* S212, *Streptococcus pyogenes* (group A), streptococci groups A,C,G, *Peptostreptococcus magnus,* and *Streptococcus agalactiae* (group B).

31. The protein of claim 30, wherein the natural bacterial receptor is staphylococcal protein A or streptococcal protein G.

32. The protein of claim 30, wherein the natural bacterial receptor is selected from the group consisting of: Fc receptor IgG type I, type II, type III, type IV, type V, and type VI; fibronectin receptor; M protein; plasmin receptor; collagen receptor; fibrinogen receptor; protein L; protein H; protein B; and protein Arp.

33. The protein of claim 30, wherein the natural bacterial receptor is the Fc receptor IgG type I of staphylococcal protein A or the serum albumin receptor of streptococcal protein G.

34. The protein of claim 28, wherein at most about 50% of the amino acid residues of the natural bacterial receptor have been substituted by other amino acid residues.

35. The protein of claim 34, wherein at most about 25% of the amino acid residues of the natural bacterial receptor have been substituted by other amino acid residues.

36. The protein of claim 35, wherein the natural bacterial receptor is staphylococcal protein A or streptococcal protein G.

37. The protein of claim 36, wherein the interaction partner is selected from the group consisting of IgF-I, IGF-II, hGH, Factor VIII, insulin, apolipoprotein, and their respective receptors.

38. The protein of claim 35, wherein the natural bacterial receptor is selected from the group consisting of: Fc receptor IgG type I, type II, type III, type IV, type V, and type VI; fibronectin receptor; M protein; plasmin receptor; collagen receptor; fibrinogen receptor; protein L; protein H; protein B; and protein Arp.

39. The protein of claim 35, wherein the natural bacterial receptor is the Fc receptor IgG type I of staphylococcal protein A or the serum albumin receptor of streptococcal protein G.

40. The protein of claim 28, wherein only surface-exposed amino acid residues of the natural bacterial receptor have been substituted.

41. The protein of claim 28, wherein the interaction partner is selected from the group consisting of a protein, lipid, carbohydrate, and inorganic substance.

42. The protein of claim 41, wherein the interaction partner is a carbohydrate.

43. The protein of claim 41, wherein the interaction partner is selected from the group consisting of IgF-I, IGF-II, hGH, Factor VIII, insulin, apolipoprotein, and their respective receptors.

44. The protein of claim 41, wherein the interaction partner is selected from the group consisting of a viral coat protein, bacterial antigen, biotin, and cell marker.

45. The protein of claim 41, wherein the interaction partner is an antibody fragment.

46. The protein of claim 41, wherein the interaction partner is an organic ligand.

* * * * *

UNITED STATES PATENT AND TRADEMARK OFFICE

CERTIFICATE OF CORRECTION

PATENT NO. : 6,534,628 B1 
DATED : March 18, 2003
INVENTOR(S) : Björn M. Nilsson, Per-Ake Nygren and Mathias Uhlen It is certified that error appears in the above-identified patent and that said Letters Patent is hereby corrected as shown below:

Column 18,
Line 2, replace "Fe" with -- Fc --.
Line 6, replace "IgG" with -- IgA --.
Line 14, replace "domain" with -- domains --.
Line 37, replace "substance" with -- substances --.

Signed and Sealed this

Thirteenth Day of January, 2004

JON W. DUDAS
*Acting Director of the United States Patent and Trademark Office*